United States Patent
Farhi et al.

(10) Patent No.: US 12,326,448 B2
(45) Date of Patent: Jun. 10, 2025

(54) COMPOSITIONS AND METHODS FOR HIGH-SENSITIVITY IMMUNOASSAYS

(71) Applicant: UNIVERSITY OF VIRGINIA PATENT FOUNDATION, Charlottesville, VA (US)

(72) Inventors: Leon S. Farhi, Charlottesville, VA (US); Alexander L. Klibanov, Charlottesville, VA (US); Bruce D. Gaylinn, Louisa, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1108 days.

(21) Appl. No.: 16/322,679

(22) PCT Filed: Aug. 7, 2017

(86) PCT No.: PCT/US2017/045745
§ 371 (c)(1),
(2) Date: Feb. 1, 2019

(87) PCT Pub. No.: WO2018/027221
PCT Pub. Date: Feb. 8, 2018

(65) Prior Publication Data
US 2021/0373011 A1 Dec. 2, 2021

Related U.S. Application Data

(60) Provisional application No. 62/371,391, filed on Aug. 5, 2016.

(51) Int. Cl.
*G01N 33/543* (2006.01)
*G01N 21/64* (2006.01)
*G01N 33/68* (2006.01)

(52) U.S. Cl.
CPC . *G01N 33/54393* (2013.01); *G01N 33/54306* (2013.01); *G01N 33/54346* (2013.01); *G01N 33/6857* (2013.01); *G01N 21/6408* (2013.01); *G01N 21/6428* (2013.01); *G01N 2021/6439* (2013.01); *G01N 2333/36* (2013.01); *G01N 2333/908* (2013.01)

(58) Field of Classification Search
CPC ............ G01N 33/6857; G01N 21/644; G01N 2021/6439; G01N 2333/36; G01N 33/5432
See application file for complete search history.

(56) References Cited

U.S. PATENT DOCUMENTS

| | | |
|---|---|---|
| 2008/0213189 A1 | 9/2008 | Lee et al. |
| 2009/0166560 A1* | 7/2009 | Dai .................. B82Y 30/00 435/7.1 |
| 2013/0183771 A1 | 7/2013 | Meltola et al. |
| 2014/0294933 A1* | 10/2014 | Cha .................... C12N 5/069 435/373 |
| 2014/0348755 A1 | 11/2014 | Weng |

FOREIGN PATENT DOCUMENTS

| | | | |
|---|---|---|---|
| CA | 2380777 C * | 1/2011 | ........... C07K 16/109 |
| WO | 2009/072074 A1 | 6/2009 | |

OTHER PUBLICATIONS

Du et al. "Lipid-Coated Gold Nanoparticles Functionalized by Folic Acid as Gene Vectors for Targeted Gene Delivery in vitro and in vivo", ChemMedChem, vol. 12, pp. 1768-1775, published 2017. (Year: 2017).*

* cited by examiner

*Primary Examiner* — Shafiqul Haq
*Assistant Examiner* — Nam P Nguyen
(74) *Attorney, Agent, or Firm* — RAPHAEL BELLUM PLLC

(57) ABSTRACT

Lanthanide chelate lipid nanoparticles, and methods of their synthesis and use are described. Biological molecules labeled with the lipid nanoparticles, useful in bioaffinity assays with improved sensitivities are also described.

21 Claims, 14 Drawing Sheets

COMPOSITIONS AND METHODS FOR HIGH-SENSITIVITY IMMUNOASSAYS

CROSS-REFERENCE TO RELATED APPLICATIONS

This application claims priority to U.S. Application No. 62/371,391, filed Aug. 5, 2016, which is incorporated herein by reference.

FIELD OF THE INVENTION

The invention generally relates to improved labels and methods for high sensitivity assays, such as immunoassays. More particularly, the invention relates to lanthanide chelate lipid nanoparticles, used as labels in high sensitivity assays.

BACKGROUND OF THE INVENTION

Immunoassays are a mainstay of the biotechnology industry, medical practice and biomedical research. Millions of immunoassays are performed annually for many clinically important disease markers, pathogens, drugs, hormones, and metabolites. Many of these tests would benefit from increased sensitivity, expanded range, or simplified procedures.

One approach to improve immunoassay technology is to apply time-resolved fluorescence (TRF), a non-radioisotope, non-enzymatic fluorescence label procedure that utilizes the unique long-lifetime fluorescence (measured in milliseconds after excitation) of certain lanthanide chelates. As a result, it is possible to excite lanthanides using a pulsed light source (Xenon flash lamp or pulsed laser for example), and measure after the excitation of any background or non-specific fluorescence has decayed. This results in lower measurement backgrounds than in standard fluorescence assays.

TRF is more sensitive than standard fluorescent labels and avoids many limitations of enzymatic amplification methods (ELISA). The long excited state lifetimes of lanthanides makes it possible to obtain high sensitivities. U.S. Pat. No. 4,565,790 discloses a method for fluorescence spectroscopic determination of a biological substance provided with a marker consisting of a lanthanide chelate complex formed by a lanthanide coupled to the substance via a chelate forming compound.

One commercially available TRF format is the Dissociation-Enhanced Lanthanide Fluorescence ImmunoAssay (DELFIA®; PerkinElmer) in which long-lasting fluorescent micelles are formed by the dissociation of the complex-bound chelate after adding a low pH enhancement solution. A typical agent-detection assay is similar to an ELISA except that the detector antibody is labeled directly with europium (Eu) instead of an enzyme. Because the detector antibody is directly labeled and the signal generated is strong, the assay can be completed in less time than a colorimetric assay that requires a timed enzyme incubation (which is temperature and pH dependent) followed by a stop reagent. However, the sensitivity of assays using the DELFIA® reagent, which consists of streptavidin labeled with only 6-8 Eu per molecule, can be improved. Liu et al, 2008 report the use of a specialized poly-HRP streptavidin to detect a fluorescent substrate showing dramatically improved sensitivity, 6 pg/ml, relative to a standard ELISA. Soukka, et al., 2001, demonstrated that by using polystyrene beads with thousands of Eu per particle, the sensitivity of TRF immunoassays could, in some particular cases, be improved. However, the polystyrene beads showed nonspecific interactions with certain polyclonal antisera.

There is a long felt need in the art for immunoassays with greater sensitivity. The present invention addresses those needs.

SUMMARY OF THE INVENTION

This invention generally relates to reagents and methods for assays with improved sensitivity. This invention relates to a new label for time resolved fluorescence bioaffinity assays. In particular, this invention relates to a lipid nanoparticle comprising:
 a) a lipid with an aliphatic chain, wherein the chain length ranges from C19 to C50, attached to a linker moiety;
 b) a lipid with an aliphatic chain, wherein the chain length ranges from C19 to C50, attached to a lanthanide chelate, wherein the lanthanide is selected from the group consisting of $Eu^{3+}$, $Tb^{3+}$, $Sm^{3+}$ and $Dy^{3+}$; and
 c) optionally, a lipid with an aliphatic chain, wherein the chain length ranges from C19 to C50.

The invention also relates to labeled biomolecules, such as antibodies, wherein the biomolecule is linked to a lipid nanoparticle of the invention. The invention also relates to a time-resolved fluorescence bioaffinity assay to determine the presence or concentration of an analyte in a sample comprising the steps of:
 a) mixing the sample with a labeled reagent, wherein the labeled reagent is a reagent linked to a lipid nanoparticle of the invention;
 b) reacting the analyte with the reagent, wherein a bioaffinity reaction between the analyte and the reagent takes place,
resulting in a reaction product, wherein the analyte is bound to the labeled reagent,
 c) separating said reaction product from unbound labeled reagents, and
 d) measuring the amount of lanthanide from the reaction product by time-resolved fluorescence.

This invention also relates to a time-resolved fluorescence bioaffinity assay to determine the presence or concentration of up to four analytes in a sample.

This invention also relates to an improved time-resolved fluorescence bioaffinity assay. In a time-resolved fluorescence bioaffinity assay where a labeled reagent is used to determine the presence or concentration of an analyte in a sample, the improvement is that the label in the labeled reagent is a lipid nanoparticle of the invention.

DETAILED DESCRIPTION

Figure 1:
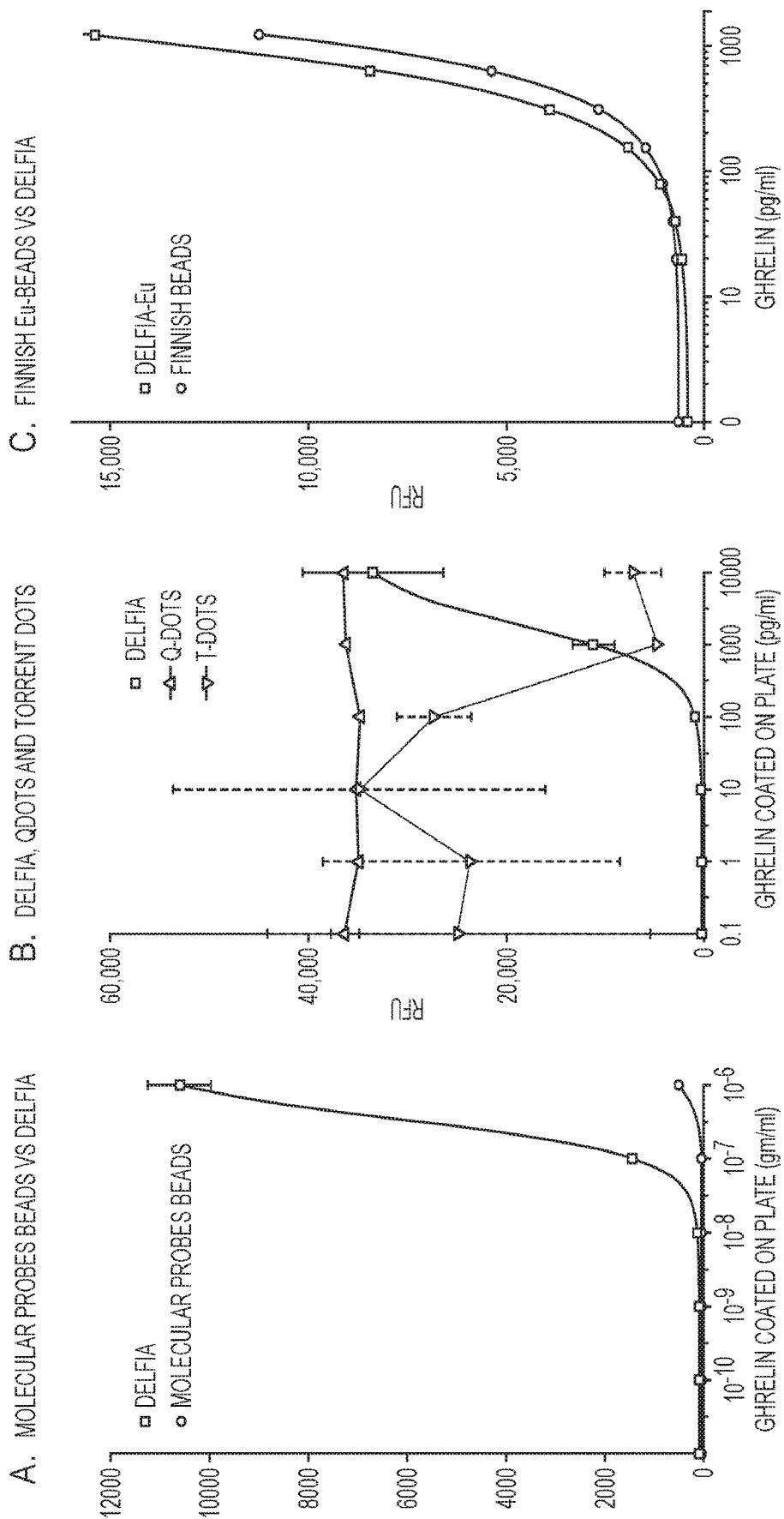
FIG. 1 shows the evaluations of four different previously available fluorescent nanoparticle preparations compared to the PerkinElmer DELFIA® in a TRF assay run in parallel to detect biotinylated antisera to ghrelin binding to different doses of ghrelin coated on a microtiter plate. A. Molecular Probes Eu filled streptavidin coated polystyrene nanoparticle beads; B. Quantum Dots from Invitrogen and Torrent Dots from BioPal; and C. polystyrene nanoparticles (Protocol from Nareoja, et al., 2009, see Example 9 below).

This invention generally relates to new labels and methods for assays with improved sensitivity. Time-resolved fluorescence (TRF) with lanthanide labels (e.g., $Eu^{3+}$) has been considered as a replacement for enzymatic amplification detection methods (ELISA). In order to avoid protein inactivation, the number of lanthanide chelates which can be coupled to an antibody or streptavidin is currently limited to less than about a dozen, thereby limiting detection sensitivity. The lipid nanoparticles of the invention carry thousands of lanthanide atoms (up to $10^4$) to improve TRF detection sensitivity.

In particular, this invention relates to a lipid nanoparticle comprising:
a) a lipid with an aliphatic chain, wherein the chain length ranges from C19 to C50, attached to a linker moiety;
b) a lipid with an aliphatic chain, wherein the chain length ranges from C19 to C50, attached to a lanthanide chelate, wherein the lanthanide is selected from the group consisting of $Eu^{3+}$, $Tb^{3+}$, $Sm^{3+}$ and $Dy^{3+}$; and
c) optionally, a lipid with an aliphatic chain, wherein the chain length ranges from C19 to C50.

The lipid can be the same or different lipid for each of the components of the nanoparticle. For example, in a lipid nanoparticle of the invention, the lipid for components a) and b) is di-C22-phosphatidylethanolamine. In another lipid nanoparticle of the invention the lipid in component a) and b) is di-C22-phosphatidylethanolamine, and the lipid in component c) is di-C22-phosphatidylcholine. When different lipids are used for components a), b), and optionally c), one skilled in the art would be able to select lipids with compatible head groups and aliphatic chains of roughly similar length, to maintain the stability of the lipid nanoparticle: it may be preferred that to improve cohesion between lipid molecules and at the same time minimize potential for phase separation of the constituent lipids, chain length and degree of saturation of the lipid anchors is similar.

Lipids are hydrophobic or amphiphilic molecules; the amphiphilic nature of some lipids allows them to form structures such as vesicles, micelles, liposomes, or membranes in an aqueous environment. The term "amphiphilic" describes a molecule carrying groups having an affinity for substances which are hydrophobic in nature and groups having an affinity for substances which are hydrophilic in nature.

The lipid components of the lipid nanoparticles of the invention are independently selected from phospholipids, sphingolipids, sulfolipids, glycerolipids, aminolipids, peptide-lipids, fatty acid derivatives, fatty alcohol derivatives, fatty aldehydes, polymer-lipids, carbohydrate-lipids, or polyol-lipids. Exemplary non-limiting phospholipids include: phosphatidic acid, phosphatidylethanolamine, phosphatidylcholine, phosphatidylserine, phosphatidylinositol phosphate, phosphatidylinositol bisphosphate, phosphatidylinositol triphosphate, ceramide phosphorylcholine (Sphingomyelin), ceramide phosphorylethanolamine (Sphingomyelin) and ceramide phosphorylglycerol. Exemplary sulfolipids include sulfoquinovosyl diacylglycerol and sulfatides. Glycerolipids include monoacylglycerols, diacylglycerols, triacyl glycerols, as well as glycosylglycerols, which with one or more sugar residues attached to glycerol via a glycosidic linkage. Examples of aminolipids include phosphatidylethanolamine, also known as 1,2-diacyl-glycero-phosphoethanolamine, which may be optically active or racemic, dialkylamines, such as di-C22-alkylamine, or other lipids that carry a primary or secondary amino group(s). Peptide lipids are formed by conjugating fatty acids to amino acids or peptides. Examples of peptide-lipids include diacyl lysine, diacyl ornitine, and peptides that contain these modified amino acids, e.g., di-(alpha, epsilon) C22-acyl-lysine-COOH or derivatives of those amino acids, as well as oligopeptides that are modified to form amides or esters or alkyl derivatives of amino acids. Fatty acids are carboxylic acids with a long aliphatic chain. Examples of fatty acid derivatives include amides or esters or nitriles, for example, di-C22-acylglycerol (ester) or triacyl glycerols, or di-C28-acylglycerol. Examples of alcohol derivatives include long-chain fatty ethers with glycerol (e.g., tri-C22-alkyl ether of sorbitol or mannitol), or with polyglycerol, or esters with oligocarboxylic acid molecules, such as DTPA or TTHA. Fatty aldehyde derivatives include Schiff base complexes between e.g., C22-aldehyde and a primary amino group-containing molecule, or a hydrazide or hydrazone derivative of such molecule. Polymer-lipids include lipids conjugated to polymers such as polyalkylethers, such as polyethylene glycol (PEG), polymethylethylene glycol, polypropylene glycol, and polyhydroxypropylene glycol. Additional suitable polymers include polyvinylpyrrolidone, polyvinyl alcohol and polyacrylic acid. Exemplary carbohydrate-lipids, or glycolipids, include, glyceroglycolipids, galactolipids, cerebrosides, galactocerebrosides, glucocerebrosides, glcosphingolipids, and gangliosides.

In a lipid nanoparticle of the invention, preferably, the lipids are phospholipids. In a lipid nanoparticle of the invention the lipids may be, for example, phosphatidylethanolamine, phosphatidylcholine and mixtures thereof.

Lipid nanoparticles of the invention have lipids with one or more aliphatic chains, where the lengths of the aliphatic chain can be from about C19 to about C50, for example, from about C22 to about C38, or from about C28 to about C32. This includes, for example, C19, 20, 21, 22, 23, 24, 25, 26, 27, 28, 29, 30, 31, 32, 33, 34, 35, 36, 37, 38, 39, 40, 41, 42, 43, 45, 46, 47, 48, 49, and 50. Generally, stability of a lipid nanoparticle, specifically, its resistance to dissolution at low concentration, is directly related to intermolecular cohesion between the lipid anchors of the constituent molecules, which can be assessed as critical micellar concentration of those molecules, i.e., the highest concentration of individual molecules of lipid/surfactant in the surrounding aqueous media, which does not result in micelle formation. It is known that critical micellar concentration of general use phospholipids (e.g., those used in liposome formulation for drug delivery systems) is between sub-nanomolar and picomolar range that CMC of DPPC (di-C16) is 0.5 nM (Ge, et al., 2001), and is even higher for di-C14 derivatives. Therefore, when hundreds of milligrams of these materials are administered to patients, lipid concentration is sufficiently high that the majority of the particles stay intact and do not release individual molecules as a significant fraction. However, application of such particles as immunoassay enhancers at very low concentrations, is not feasible as they may dissolve/degrade and not achieve the desired goal of retaining a high number of lanthanides per particle.

Lipid nanoparticles of the invention comprise lipids with one or more aliphatic chains. For example, the lipids may have 1, 2, 3, 4, 5, 6, 7, 8, 9, or 10 aliphatic chains. Preferably, the lipid has 1, 2, 3 or 4 aliphatic chains. In a lipid nanoparticle of the invention, the lipid has 2 aliphatic chains. When more than one lipid aliphatic chains are present, the chains do not have to be the same length. Preferably, the chains are of the same length. The aliphatic chains may be saturated or unsaturated. Preferably the aliphatic chains are saturated. The aliphatic chains may be branched or linear. Preferably, the chains are linear.

In a lipid nanoparticle of the invention, the lipid is preferably selected from the group consisting of di-C22-phosphatidylethanolamine, di-C22-phosphatidylcholine, di-C22-phosphatidylglycerol, di-C22-phosphatidylinositol, di-C22-phosphatidylserine, di-C22-phosphatidic acid and/or esters thereof, di-C22-alkylamine, di-C22-acylglyceride esters, hydroxy- or methoxy-(PEG)-Di-C22-phosphatidylethanolamine, (such as hydroxy- or methoxy-(PEG)$_{12}$-Di-C22-phosphatidylethanolamine), di-C22-acyl glycerol, and tri-C22-acyl glycerol.

In lipid nanoparticles according to the invention, the purpose of the "linker moiety" is to either covalently or non-covalently attach the lipid nanoparticle to a bioaffinity reagent. A preferred lipid nanoparticle of the invention is a lipid nanoparticle wherein biotin is the linker moiety. Such a lipid nanoparticle can non-covalently attach to streptavidin with high affinity, resulting in a labeled streptavidin of the invention. Lipid nanoparticles with biotin linker moieties also bind with high affinity to neutravidin and avidin. Because streptavidin has four identical biotin binding units, the lipid nanoparticle of the invention with biotin as the linker moiety, or a labeled streptavidin of the invention can be flexibly used in bioaffinity assays. For example, in a bioaffinity assay of the invention in the form of a sandwich immunoassay for the detection of an analyte, a labeled streptavidin can be used to bind to a biotinylated reporter antibody. Alternatively, streptavidin can be added first to the reaction mixture to bind to the biotinylated reporter antibody, and then the lipid nanoparticle can be added subsequently, to bind to the streptavidin. Indeed, lipid nanoparticles with biotin linker moieties can be used to detect the presence of any other biotinylated molecule. For example, if any biotinylated molecule is present on a surface, adding streptavidin will result in the streptavidin bound to the biotin, and the streptavidin will still have open binding sites to bind additional biotins. Subsequent addition of a lipid nanoparticle of the invention with biotin as the linker moiety will result in the nanoparticle binding to the streptavidin.

Attachment of the linker moiety to a lipid can be performed by methods and reagents known in the art. For example, many linker groups are available as N-hydroxysuccinimide conjugates, which can react with to an amine group on a lipid, such as phosphatidylethanolamine. NHS-PEG-biotin linkers are commercially available, for example from MILLIPORE SIGMA.

Alternatively, a "covalent linker moiety" serves to covalently attach the lipid nanoparticle to a bioaffinity reagent. Gallego, et al., 2014, incorporated herein by reference in its entirety, summarizes strategies to functionalize the surface of liposomes for improved targeting of drug-carrier nanosystems. Well-established chemical reactions have been applied to attach different moieties to a lipid or to the surface of preformed liposomes, including amine-carboxylic acid conjugation, disulfide bridge formation, hydrazone bond formation, and the thiol-maleimide addition reaction yielding a thioether bond, and bioorthogonal chemistry methods have been reported more recently. The strategies in Gallego, et al., 2014, can be used to prepare lipid nanoparticles of the invention. For example, classical strategies to covalently attach lipids with a linker moiety to another molecule include: a) crosslinking of primary amines by glutaraldehyde, for lipids with an amine as a linker moiety, (b) carbonyl-amine bond formation, for lipids with carboxylic acid or succinimidyl esters as linker moieties, (c) amide bond formation, for lipids with a para-nitrophenylcarbonyl as a linker moiety, (d) disulfide bond formation, for lipids with a thiol as a linker moiety, (e) thioether bond formation by the maleimide-thiol addition reaction, for lipids with a maleimide as a linker moiety, and (f) hydrazone bond formation, for lipids with an aldehyde as a linker moiety. More modern strategies include Copper(I)-Catalyzed Huisgen 1,3-Dipolar Cycloaddition (CuAAC), Copper-Free Click Chemistry, The Staudinger Ligation, and Tetrazine/Trans-Cyclooctene Inverse Electron Demand Diels-Alder Cycloaddition (IEDDA). (See Gallego et al., 2014.)

For component a) the covalent linker moiety may be selected from maleimide, vinylsulfone, thiopyridine, isothiocyanate, trans-cyclooctene, dibenzoyclooctyl, azide, alkyne, imidazolylcarbonyl, tetrazine, iodoacetamido, bromoacetamido, succinimidyl, pentachlorophenyl, tetrafluorophenyl, sulfosuccinimdyl, carboxylic acid, para-nitrophenylcarbonyl, thiol, and aldehyde. Once the covalent linker moiety reacts with its a biological molecule with an appropriate corresponding group, the resulting bonds include: amide, hydrazide, hydrazone, Schiff base, reduced Schiff base, ester, isourea, thiourea, sulfonamide, thioether, thio-ester, and disulfide.

In a preferred lipid nanoparticle of the invention, the covalent linker moiety is maleimide. Lipid nanoparticles of the invention with maleimide as the linker moiety can be added in aqueous saline, under inert gas atmosphere, e.g., Argon gas, devoid of oxygen, to an antibody, e.g., IgG solution in buffer where antibody may be subjected to partial breakage by disulfide bonds by e.g., tris(2-carboxyethyl) phosphine reagent, and incubated, so that a reaction of maleimide with thiol could take place. Free unreacted antibody can be removed by ultra/diafiltration, dialysis, centrifugation, or size exclusion chromatography. Heterobifunctional reagents can also be used to assist covalently attachment of the lipid nanoparticle to a biomolecule. For example, N-succinimidyl 3-(2-pyridyldithio)propionate (SPDP) has an N-hydroxysuccinimide ester group which reacts with amino groups and a 2-pyridyl disulphide structure which reacts with aliphatic thiols. A protein or antibody can be incubated with SPDP or iminothiolane to generate disulfide bonds or thiols, by reaction with primary amino groups on the protein surface, followed by reaction with a lipid nanoparticle of the invention with maleimide as the linker moiety.

In some lipid nanoparticles of the invention linker moiety in component a) is directly attached to the lipid. In other lipid nanoparticles of the invention, the linker moiety in component a) is attached to the lipid via a polyethylene glycol based linker, wherein the polyethylene glycol (PEG) based linker is (—$CH_2$—$CH_2$—O)$_n$, wherein n is an integer from 3-2000. Longer PEGs can provide better surface protection to inhibit non-specific binding. Ranges of PEG lengths, include, but are not limited to about 3 to about 2,000, about 10 to about 1,500, about 12 to about 1,000, about 15 to about 500, about 20 to about 250, about 25 to about 150, and about 80 to about 100. PEG lengths useful in the invention include, but are not limited to, 3, 4, 5, 6, 7, 8, 9, 10, 11, 12, 13, 14, 15, 16, 17, 18, 19, 20, 21, 22, 23, 24, 25, 80, 100, 150, 200, 250, 300, 350, 500, 1000, 1,500, and 2,000.

Numerous hetero-bifunctional molecules with PEG linkers of various lengths are commercially available, for example from MILLIPORE-SIGMA®, and can be used to prepare component a). Such molecules can be chosen based on the bioaffinity reagent and lipid. Non-limiting examples include: azide-PEG-amine ($N_3$-PEG-$NH_2$), azide-PEG-NHS Ester, biotin-PEG-maleimide, biotin-PEG-NHS ester, biotin-PEG-amine (Biotin-PEG-$NH_2$), biotin-PEG-COOH, maleimide-PEG-biotin, maleimide-PEG-NHS ester, maleimide-PEG-COOH, Maleimide-PEG-formyl (Maleimide-PEG-CHO), thiol-PEG-amine, thiol-PEG-COOH, and the like, available in various PEG lengths.

Exemplary lipid derivatives for use as component a) include: biotin-(PEG)$_{12}$-di-C22-phosphatidylethanolamine, biotin-(PEG)$_3$-Di-C22-phosphatidylethanolamine, maleimide-(PEG)$_{12}$-Di-C22-phosphatidylethanolamine, and trans-cyclooctene-(PEG)$_{12}$-Di-C22-phosphatidylethanolamine.

In lipid nanoparticles of the invention, component b) is a lipid attached to a lanthanide chelate. The lanthanide chelate comprises a chelating agent and a lanthanide ion selected from $Eu^{3+}$, $Tb^{3+}$, $Sm^{3+}$ and $Dy^{3+}$. A lanthanide chelating agent for use in the lipid nanoparticles of the invention comprises two parts—a chelating group for binding the lanthanide ion and some functionality to bind to the lipid. Trivalent lanthanide cations are hard Lewis acids with a coordination number of 8-9, requiring hard donors, for example carboxylates, β-diketonates and phosphonates, which contain nitrogen and oxygen donor atoms. The lanthanide chelate should have sufficient stability under the intended assay conditions, and therefore necessitates the use of multidentate chelators.

Non-limiting, suitable chelating agents for component b) include diethylenetriamine pentaacetic acid (DTPA), ethylenediamine tetraacetic acid (EDTA), triethylenetetraminehexaacetic acid (TTHA), 1,4,7,10-tetraazacyclododecane-1,4,7,10-tetraacetic acid (DOTA), 1,4,7-triazacyclononane-N,N',N"-triacetic acid (NOTA), deferoxamine, diethylenetriamine penta(methylene phosphonic acid) (DTPMP), 1,4,7,10-tetraaza-1,4,7,10-tetra(2-carbamoylmethyl)cyclododecane (TCMC), 1,4,7,10-Tetraazacyclododecane-1,4,7-tri(carbamoylmethyl)-10-acetic acid (DOTAM), 2-[1,4,7,10-Tetraazacyclododecane-4,7,10-tris(t-butyl acetate)]-pentanedioic acid (DOTAGA), 1,4,8,11-tetraaza-cyclotetradecane-1,4,8-triacetic acid (DO3A), tetraazabicyclopentadecatrienetriacetic acid (PCTA), and 1,4,7-Triazacyclononane-1,4-bis(acetic acid) (NO2A). In a lipid nanoparticle of the invention, a preferred chelating agent is DTPA.

The chelating agent in the lipid nanoparticle of the invention is covalently attached to the lipid. Methods and reagents to attach chelating agents to lipids are known in the art. For example, bifunctional chelators, and various derivatives thereof are available from Macrocyclis™, such as S-2-(4-isothiocyanatobenzyl)-diethylenetriamine pentaacetic acid, (p-SCN-Bn-DTPA). With this isothiocyanate derivative of DTPA, the NCS reacts with an amino group present on a lipid, e.g., phosphatidylethanolamine, and forms a thiourea bond. Alternatively, DTPA is attached to phosphatidylethanolamine via one of its carboxyls, forming an amide bond.

Lanthanides are any of the series of fifteen metallic elements from lanthanum to lutetium in the periodic table. In a lipid nanoparticle according to the invention, the lanthanide is selected from $Eu^{3+}$, $Tb^{3+}$, $Sm^{3+}$ and $Dy^{3+}$. For example, in a lipid nanoparticle according to the invention the lanthanide is $Eu^{3+}$ or $Tb^{3+}$. In a preferred lipid nanoparticle of the invention, the lanthanide is $Eu^{3+}$. The simultaneous use of two or more lanthanides allows for two or more bioaffinity assays to be carried out using the same sample and assay mixture by labeling the reagents of each assay with a different lanthanide.

Non-limiting examples of lipid derivatives for use as component b) include: europium-DTPA-di-C22-phosphatidylethanolamine, terbium-DTPA-di-C22-phosphatidylethanolamine, dysprosium-DTPA-di-C22-phosphatidylethanolamine, samarium-DTPA-di-C22-phosphatidylethanolamine, europium-TTHA-di-C22-phosphatidylethanolamine, terbium-TTHA-di-C22-phosphatidylethanolamine, dysprosium-TTHA-di-C22-phosphatidylethanolamine, and samarium-TTHA-di-C22-phosphatidylethanolamine, europium-DOTA-di-C22-phosphatidylethanolamine, terbium-DOTA-di-C22-phosphatidylethanolamine, dysprosium-DOTA-di-C22-phosphatidylethanolamine, and samarium-DOTA-di-C22-phosphatidylethanolamine.

In lipid nanoparticles of the invention when component c) is present, the component is a lipid. In a lipid nanoparticle of the invention the lipid of component c) is pegylated, where PEG is covalently attached to the polar head of the lipid, for example, (PEG)$_{12}$-carboxylate forming an amide bond with the primary amino group of phosphatidylethanolamine. In lipid nanoparticles of the invention, exemplary lipids for use as component c) include: di-C22-phosphatidylethanolamine, di-C22-phosphatidylcholine, (PEG)$_{12}$-di-C22-phosphatidylethanolamine, and (PEG)$_{12}$-di-C22-phosphatidylcholine.

Lipid nanoparticles of the invention provides a stronger fluorescence signal per analyte than commercially available Eu-labeled streptavidin. Lipid nanoparticles of the invention carry thousands of lanthanide chelates per nanoparticle.

The weight to weight ratios of component a):component b) range from about 100:1 to about 1:100, for example from about 10:1 to about 1:10, for example from about 5:1 to about 1:5, for example from about 2:1 to about 1:2. In a preferred lipid nanoparticle according to the invention, the weight to weight ratio of component a):component b) is about 1:1.

When component c) is present in the lipid nanoparticle, the weight to weight ratio of the (total amount of component a) plus component b)):component c) ranges from about 200:1 to about 1:100, for example from about 20:1 to about 1:10, for example from about 10:1 to about 1:5, for example from about 4:1 to about 1:2. In a preferred lipid nanoparticle of the invention the weight to weight ratio of the (total amount of component a) plus component b)):component c) is about 10:1.

The lipid nanoparticles of the invention have a mean size from about 10 to 1000 nanometers, for example, from about 20 nm to 800 nm, from about 30 nm to 600 nm, from about 40 nm to 400 nm, from about 50 nm to 200 nm. Preferably, the lipid nanoparticles have mean size from about 90 nm to 150 nm.

Lipid nanoparticles according to the invention may be prepared using various combinations of components a), b), and optionally c). A lipid nanoparticle of the invention, NP1, comprises biotin-(PEG)$_3$-di-C22-phosphatidylethanolamine, Eu-DTPA-di-C22-phosphatidylethanolamine, and di-C22-phosphatidylcholine. Another lipid nanoparticle of the invention, NP2 comprises biotin-(PEG)$_{12}$-di-C22-phosphatidylethanolamine and Eu-DTPA-di-C22-phosphatidylethanolamine. Another lipid nanoparticle of the invention comprises TCO-(PEG)$_{12}$-di-C22-phosphatidylethanolamine and Eu-DTPA-di-C22-phosphatidylethanolamine. Another lipid nanoparticle of the invention comprises biotin-(PEG)$_{12}$-di-C22-phosphatidylethanolamine and Tb-DTPA-di-C22-phosphatidylethanolamine.

The invention also relates to labeled biomolecules, wherein the biomolecule is labeled with a lipid nanoparticle of the invention. Proteins, peptides, oligonucleotides and DNA labeled with lipid nanoparticles of the invention are biomolecules of the invention. Suitable biomolecules include: monoclonal, polyclonal, engineered or fragment antibody; receptor, ligand, natural binding protein; enzyme, peptide, lectin, streptavidin or avidin; oligonucleotide, polynucleotide, a cell, cell fragment, DNA, RNA cDNA, mRNA, PNA or aptamer; hapten, antigen, or hormone. Labeled biomolecules of the invention can serve as labeled reagents in a bioaffinity assay.

Figure 9:
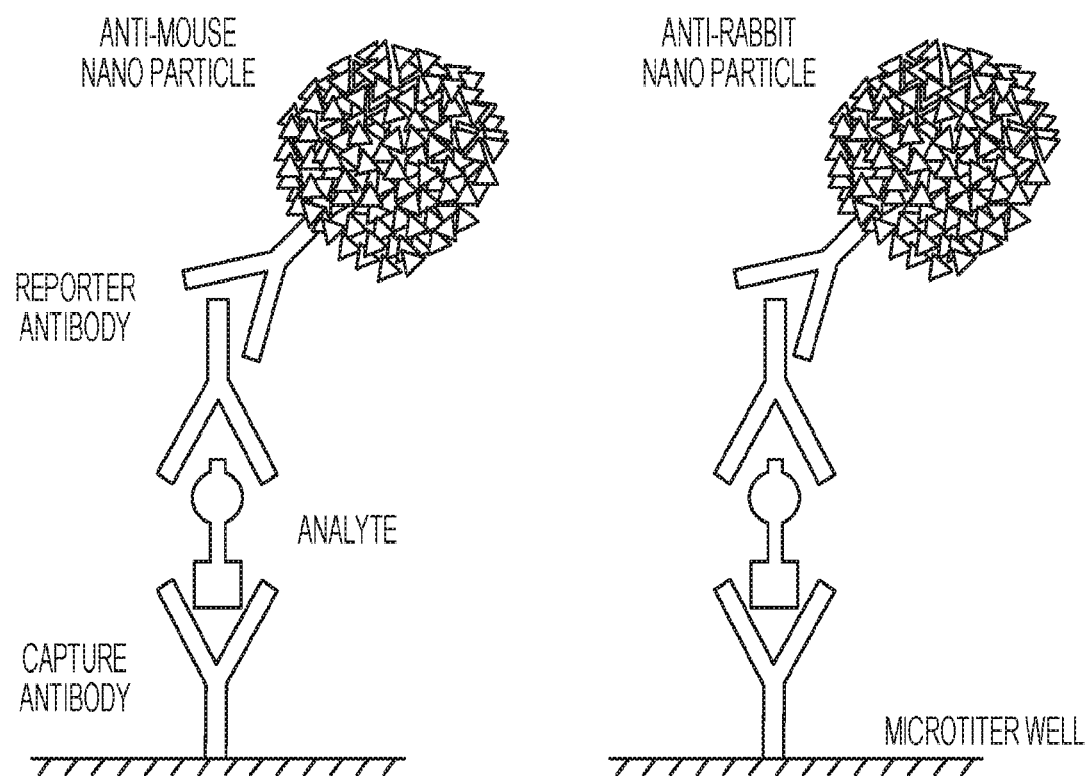
FIG. 9 is a schematic of sandwich assays showing uses of antibodies linked to lipid nanoparticles for TRF detection of rabbit or mouse antisera.

A preferred labeled biomolecule of the invention is an antibody labeled with a lipid nanoparticle of the invention. An antibody, as is known in the art, refers to a polypeptide or complex of polypeptides, substantially encoded by an immunoglobulin gene or immunoglobulin genes, or fragments thereof. Typically, an antibody is an immunoglobulin having an area on its surface or in a cavity that specifically binds to and is thereby defined as complementary with a particular spatial and polar organization of another molecule. Antibodies can be polyclonal or monoclonal. Antibodies may include a complete immunoglobulin or fragments thereof. Fragments thereof may include Fab, Fv and F(ab')$_2$, Fab', and the like. Antibodies may also be single chain antibodies. Antibodies may also include chimeric antibodies or fragment thereof made by recombinant methods. The lipid nanoparticle of the invention can be cross-linked to different kinds and species of antibodies to allow species-specific enhanced detection of reporter antisera. In a labeled antibody of the invention, the antibody is selected from anti-human, anti-mouse, and anti-rabbit antibodies. FIG. 9 shows a schematic with antibodies covalently linked to lipid nanoparticles of the invention for detection of rabbit and mouse reporter antisera in a sandwich assay.

A labeled antibody of the invention is an antibody that is linked to a lipid nanoparticle of the invention. The antibody may be covalently linked to the lipid nanoparticle or antibody may be biotinylated and the linker group of the nanoparticle may be biotin, as described above, and the antibody and nanoparticle may be crosslinked with streptavidin. Or, the lipid nanoparticle, with a covalent linker moiety, not biotin, may be covalently bound to streptavidin, and a biotinylated antibody may bind to the streptavidin. Standard reagents for biotinylation of antibodies are known in the art, for example, EZ-Link Sulfo-NHS-Biotin (Thermo Fisher Scientific).

Figure 7:
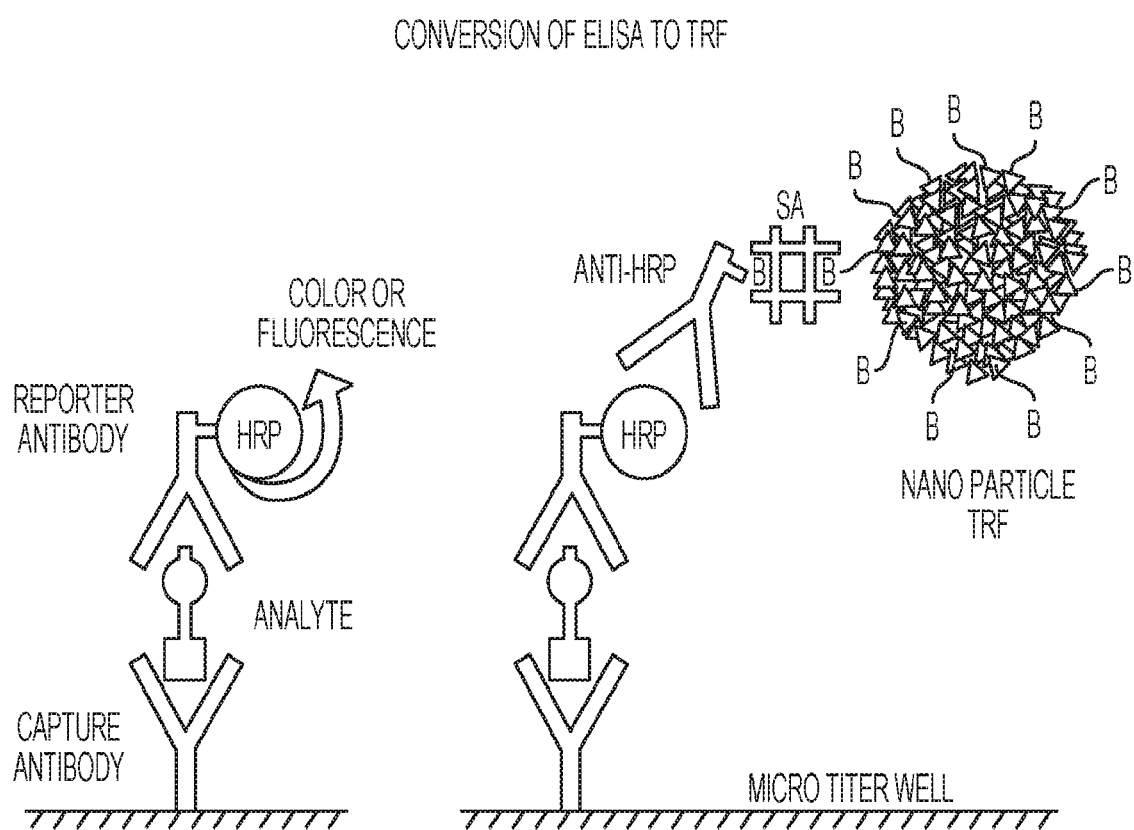
FIG. 7 is a schematic of a conversion of a standard ELISA sandwich assay (left) to a biotinylated lipid nanoparticle method for detecting HRP (right), with the lipid nanoparticle, with biotin as a linker moiety, and biotinylated anti-HRP antibody crosslinked with streptavidin.
Figure 8:
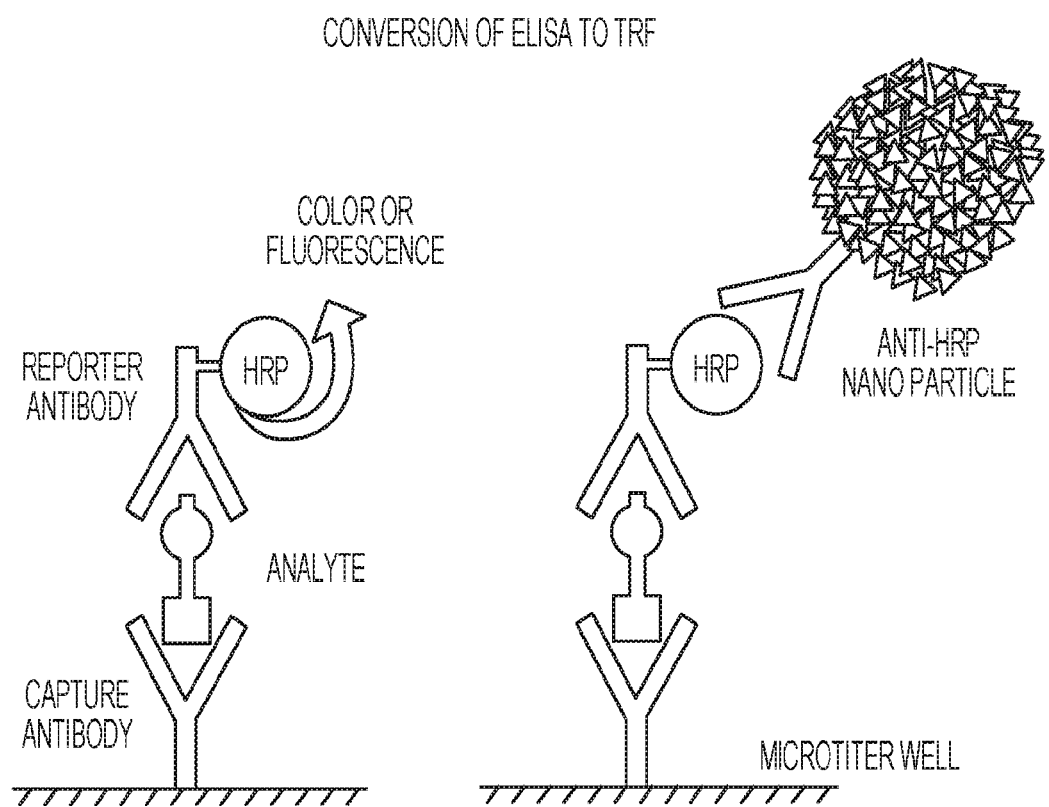
FIG. 8 is a schematic of a conversion of a standard ELISA sandwich assay (left) to a lipid nanoparticle method for detecting HRP (right), with the lipid nanoparticle covalently linked to an anti-HRP antibody.

A preferred labeled antibody according to the invention is a labeled antibody against horseradish peroxidase (anti-HRP). Anti-HRP antibodies are commercially available, e.g., goat and rabbit anti-horseradish peroxidase from Jackson ImmunoResearch Inc. In a labeled anti-HRP of the invention, the anti-HRP is biotinylated, and crosslinked with streptavidin with a lipid nanoparticle of the invention with biotin as the linker moiety. The right panel of FIG. 7 shows a schematic of a biotinylated anti-HRP antibody bound to streptavidin, bound to a lipid nanoparticle of the invention with biotin as the linker moiety. In another labeled anti-HRP of the invention, the HRP is covalently linked to a lipid nanoparticle of the invention. A lipid nanoparticle of the invention is covalently attached to the anti-HRP using a suitable linker moiety, such as a maleimide or succinimidyl to bind to, for example, a thiol or primary amine on the antibody. The right panel of FIG. 8 shows a schematic of an anti-HRP covalently linked to a lipid nanoparticle of the invention.

Figure 10:
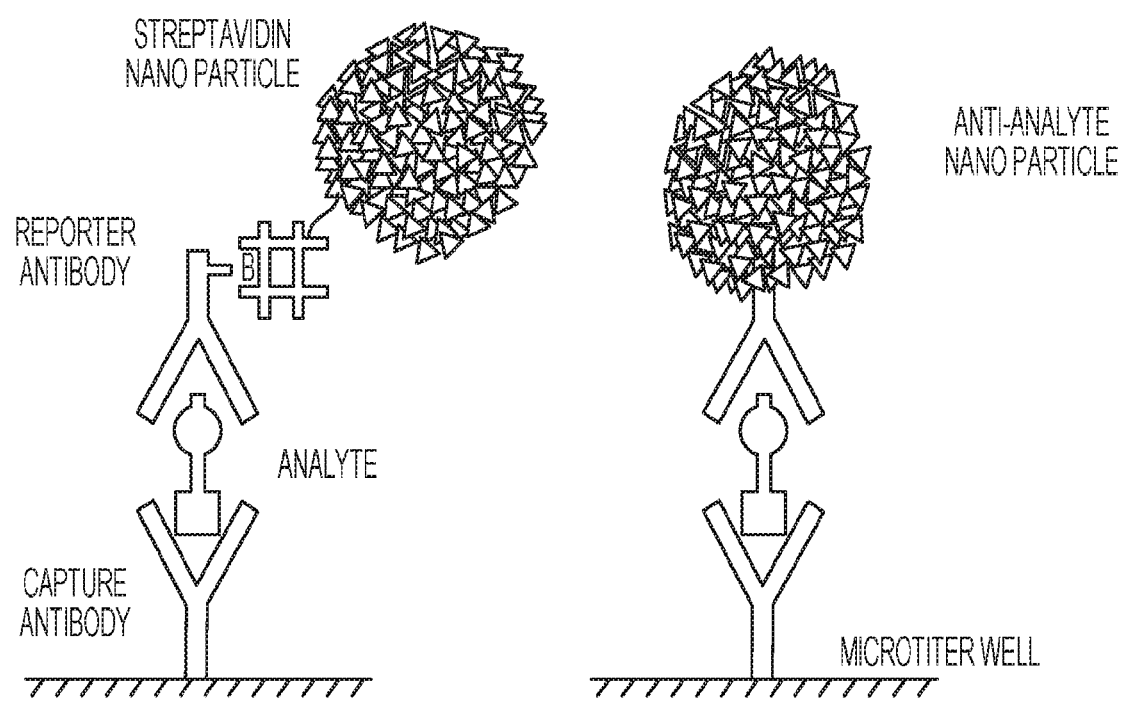
FIG. 10 is a schematic of a sandwich TRF assay showing a biotinylated reporter antibody bound to streptavidin covalently linked to a lipid nanoparticle (left) and reporter antibody covalently linked to a lipid nanoparticle (right).

Another preferred labeled biomolecule of the invention is a labeled streptavidin attached to a nanoparticle of the invention. In a labeled streptavidin of the invention streptavidin is bound to the lipid nanoparticle with biotin as the linker moiety via the high affinity streptavidin-biotin interaction. In another labeled streptavidin of the invention streptavidin is covalently linked to the lipid nanoparticle of the invention, shown in FIG. 10 (left). The labeled streptavidin of the invention is used to bind to any other biotinylated molecule in bioaffinty assays.

Another labeled biomolecule of the invention is a labeled oligonucleotide attached to a nanoparticle of the invention. In a labeled oligonucleotide of the invention the oligonucleotide biotinylated and bound to a lipid nanoparticle of the invention with biotin as the linker moiety via the high affinity streptavidin-biotin interaction. In another labeled oligonucleotide of the invention, the oligonucleotide is covalently linked to the lipid nanoparticle of the invention. For example, amine or thiol terminated oligonucleotides can form bonds with lipid nanoparticles of the invention with succinimidyl or maleimide linker moieties.

The lipid nanoparticles of the invention can be used in a variety of bio affinity assays for a variety of targets, using TRF detection. Peptides and proteins that can be assayed include, but are not limited to, cardiac troponin, C-peptide, ghrelin, growth factors, cytokines, antibodies, peptide hormones, and peptides and proteins for which commercial assays are available for use in research or for clinical diagnostic purposes.

A TRF bioaffinity assay according to the invention to determine the presence or concentration of an analyte in a sample comprises the steps of:
 a) mixing the sample with a labeled reagent, wherein the labeled reagent is a reagent linked to a lipid nanoparticle of the invention;
 b) reacting the analyte with the reagent, wherein a bioaffinity reaction between the analyte and the reagent takes place,
resulting in a reaction product, wherein the analyte is bound to the labeled reagent,
 c) separating said reaction product from unbound labeled reagents, and
 d) measuring the amount of lanthanide from the bound labeled reagent by time-resolved fluorescence. In a time-resolved fluorescence bioaffinity assay where a labeled reagent is used to determine the presence or concentration of an analyte in a sample, the improvement is that the label in the labeled reagent is a lipid nanoparticle of the invention.

In assays of the invention, the labeled reagent is a biomolecule selected from monoclonal, polyclonal, engineered or fragment antibody; receptor, ligand, natural binding protein; enzyme, peptide, lectin, streptavidin or avidin; oligonucleotide, polynucleotide, a cell, cell fragment, DNA, RNA cDNA, mRNA, PNA or aptamer; hapten, antigen, or hormone, linked to a lipid nanoparticle of the invention, either covalently, or through crosslinking with streptavidin. When the labeled reagent is an antibody, the antibody is linked to a lipid nanoparticle of the invention, either covalently or through crosslinking with streptavidin. Analytes may be selected from haptens, antigens, hormones, proteins, peptides, drugs, viruses, DNAs, RNAs, microbes, environmental toxins, cells, or cell fragments.

A "sample," refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

The bioaffinity reaction results in a reaction product between the labeled reagent and analyte. In an assay of the invention the bioaffinity reaction is a result of specific recognition of the analyte by the labeled reagent. In an assay of the invention, the reaction product is, for example, an antibody-antigen pair, a protein-ligand complex, a hybridized oligonucleotide, an aptamer-target pair, a target receptor complex, etc., as is known in the art.

In an assay of the invention, separation of bound and unbound labeled reagent can be achieved through immobilization of the analyte onto a solid support, and unbound labeled reagent is washed away. Immobilization may be through covalent attachment onto the solid support or via a capture reagent such as a capture antibody. Alternatively, the analyte is biotinylated and immobilized on a solid support coated with streptavidin. As used herein, the term "solid support" relates to a solvent insoluble substrate that is capable of forming linkages (preferably covalent bonds) with various compounds. The support can be without limitation, an acrylamide derivative, agarose, cellulose, nylon, silica, or magnetized particles. For example, suitable solid supports include, for example, beads, a microtiter plate, a nitrocellulose membrane, a glass substrate, a strip for a lateral flow assay, and the like.

An assay according to the invention is an immunoassay using a labeled antibody of the invention. For example, an immunoassay according to the invention is a sandwich immunoassay. Typically, a sandwich immunoassay is used to detect an antigen (target or analyte) with the use of a capture antibody attached a surface and a reporter antibody, forming a "sandwich." The reporter antibody binds the antigen at a different epitope than the capture antibody. Epitopes are small chemical groups on the antigen molecule that can elicit and react with an antibody; most antigens have many epitopes. The reporter antibody itself is detected directly if it is labeled. In other configurations, the reporter antibody itself is detected indirectly by another labeled antibody with binds to the reporter antibody. In an ELISA configuration of the sandwich assay, the reporter antibody is attached to an enzyme, and an enzymatic substrate is added to produce a colored, luminescent or fluorometric signal.

Each assay disclosed herein using a nanoparticle of the invention as a label, is a separate embodiment of the invention.

In a TRF immunoassay according to the invention, a labeled antibody is linked to a lipid nanoparticle of the invention, either covalently, or through crosslinking with streptavidin, as discussed above. The assay to determine the presence or concentration of an analyte in a sample comprises:
 binding the analyte on a surface;
 forming an ordered binary complex comprising the analyte and labeled antibody;
 washing off unbound reagent; and
 detecting the amount of lanthanide retained on the surface.

In a TRF sandwich immunoassay according to the invention, a labeled reporter antibody is linked to a lipid nanoparticle of the invention, either covalently or through crosslinking with streptavidin. The assay to determine the presence or concentration of an analyte in a sample comprises:
 mixing the sample, with a capture antibody immobilized on a surface, and the labeled reporter antibody;
 forming an ordered ternary complex comprising the capture antibody, the analyte and the labeled reporter antibody;
 washing off unbound reagents; and
 detecting the amount of lanthanide retained on the surface.

In another TRF sandwich immunoassay, the reporter antibody is biotinylated, and the streptavidin and lipid nanoparticle of the invention are applied sequentially. The assay to determine the presence or concentration of the analyte in a sample comprises the steps of:
 mixing the sample with a capture antibody immobilized on a surface, and a biotinylated reporter antibody;
 forming an ordered ternary complex comprising the capture antibody, the analyte, and the biotinylated reporter antibody;
 washing off unbound reagents;
 adding a streptavidin;
 forming an ordered quaternary complex comprising the capture antibody, the analyte, the biotinylated reporter antibody, and the streptavidin;

washing off unbound reagents;
adding a lipid nanoparticle of the invention with biotin as a linker moiety;
forming an ordered quinary complex comprising the capture antibody, the analyte, the biotinylated reporter antibody, the streptavidin, and the lipid nanoparticle;
washing off unbound reagents; and
detecting the amount of lanthanide retained on the surface.

The sequential application of streptavidin followed by a lipid nanoparticle of the invention with biotin as a linker moiety is not limited to sandwich immunoassays. Any bioinylated molecule, for example, a biotinylated analyte or any biotinylated molecule bound to an analyte can be detected. TRF assays according to the invention for detection of any biotinylated molecule on a surface include the steps of:
adding a streptavidin;
forming an ordered binary complex comprising the biotinylated molecule, and the streptavidin;
washing off unbound reagents;
adding a lipid nanoparticle of the invention, with biotin as a linker moiety;
forming an ordered ternary complex comprising biotinylated molecule, the streptavidin, and the lipid nanoparticle;
washing off unbound reagents; and
detecting the amount of lanthanide retained on the surface.

In another TRF sandwich assay according to the invention, labeled antisera to the reporter antibody is linked to a lipid nanoparticle of the invention, either covalently or through crosslinking with streptavidin. The assay to determine the presence or concentration of an analyte in a sample comprises:
mixing the sample with a capture antibody immobilized on a surface, and a reporter antibody;
washing off unbound reporter antibody;
forming an ordered quaternary complex comprising the capture antibody, analyte, reporter antibody, and labeled antisera;
washing off unbound reagent; and
detecting the amount of lanthanide retained on the surface.

In another TRF sandwich immunoassay according to the invention, the reporter antibody is conjugated to HRP, and a labeled anti-HRP of the invention is linked to a lipid nanoparticle of the invention, either covalently or through crosslinking with streptavidin. The assay to determine the presence or concentration of an analyte in a sample comprises:
mixing the sample with a capture antibody immobilized on a surface, and the HRP-conjugated reporter antibody;
washing off unbound reporter antibody;
forming an ordered quaternary complex comprising the capture antibody, analyte, HRP-conjugated reporter antibody, and labeled anti-HRP;
washing off unbound reagent; and
detecting the amount of lanthanide retained on the surface.

An immunoassay according to the invention is a lateral flow format. Rundstrom, et al. 2007 describes a lateral flow immunoassay using europium (III) chelate microparticles and time resolved fluorescence, using polystyrene beads. An assay using lipid nanoparticles of the invention is more sensitive than an assay using polystyrene beads. See FIG. 1 and FIG. 2.

Another assay of the invention is a nucleic acid hybridization assay. Hybridization assay are well known in the art. U.S. Pat. No. 5,256,535 discloses a method of detection of a nucleotide sequence of a nucleic acid in a sample comprising the steps: (i) contacting under hybridization condition the single stranded form of the nucleotide sequence with a single stranded nucleic acid probe, in which plurality of rare earth metal chelate groups is covalently linked via a water-soluble polymer of non-nucleic acid structure to a nucleotide acid that as one of its strand has the nucleotide sequence to be detected and as the other strand the nucleotide sequence of the probe, and (ii) detecting the formation of double stranded nucleic acid. In a hybridization assay of the invention labeled oligonucleotides are linked to a lipid nanoparticle of the invention, either covalently or through crosslinking with streptavidin as discussed above.

The simultaneous use of two or more lipid nanoparticles having different lanthanide elements allows for two or more bioaffinity assays to be carried out using the same sample and assay mixture by labeling the reagents of each assay with a different lanthanide. A TRF bioaffinity assay according to the invention to simultaneously determine the presence or concentration of one to four analytes within a sample comprises the steps of:
a) mixing the sample with one to four analyte-specific labeled reagents, wherein each labeled reagent is linked to a lipid nanoparticle of the invention, each with a different lanthanide;
b) reacting the analytes with the analyte-specific labeled reagents, wherein specific bioaffinity reactions between the analytes and their corresponding labeled reagents takes place, resulting in one to four reaction products, wherein each analyte is its specific labeled reagent,
c) separating said reaction products from unbound labeled reagents, and
d) measuring the amount of each lanthanide from the reaction products by time-resolved fluorescence.

An analyte specific reagent is one that specifically binds to the analyte through a bioaffinity reaction. The term "specifically binds to" is meant when a compound or ligand functions in a binding reaction or assay conditions which is determinative of the presence of the compound in a sample of heterogeneous compounds. The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

Assays according to the invention are generally at least about 5-fold more sensitive than the state of the art assays in use before this invention was made, for example, the best commercial C-peptide ELISA assay. An assay of the invention is at least about 10-fold more sensitive. For example, the assay with NP1 of the invention is about 20-fold more sensitive than a previous assay for ghrelin. The commercial DELFIA® assay for ghrelin is more sensitive than other assays, using polystyrene beads and particles. See FIG. 1. Assays according to the invention can be 5-fold or more sensitive than commercially available assays, for example, 10, 15, 20, 25, 30, 35, 40, 45, 50, 55, 60, 65, 70, 75, 80, 85, 90, 95, 100, 125, 150, 175, 200, 250, 300, 350, 400, 500, 750, and 1000-fold more sensitive than commercially available assays.

The following non-limiting examples will serve to illustrate the practice of the instant invention. While this invention has been disclosed with reference to specific embodiments, it is apparent that other embodiments and variations of this invention may be devised by others skilled in the art without departing from the true spirit and scope of the invention.

EXAMPLES

Example 1

Synthesis of Lipids 15.5 mg of di-C22-PE (1,2 di-C22-sn-Glycero-3-Phosphoethanolamine, Avanti Polar Lipids) was weighed directly into 20 ml glass vial, and chloroform was added to the same vial. The vial was immersed into the hot water to facilitate dissolution of the lipid in chloroform. A transparent solution had formed containing Di-C22-PE in concentration approximately 5 mg/ml.

Reaction A: Synthesis of Biotinylated Di-C22-Lipid 0.5 mg of Biotin-(PEG)$_3$-NHS (Solulink) was weighed directly into a polypropylene Eppendorf tube, 100 μl of 5 mg/ml Di-C22-PE in chloroform and 0.3 μl of N,N-Diisopropylethylamine (Aldrich) was added to the same tube; vortexed and heated this tube in hot water to completely dissolve brownish solid of Biotin-(PEG)$_3$-NHS.

The tube was left for approximately 24 hours at temperature of 60° C. In 24 hours all solvent had evaporated, leaving behind yellowish solid, which very easily dissolved when 100 μl of chloroform was added to it.

A similar reaction was performed using Biotin-(PEG)$_{12}$-NHS (Quanta Biodesign Ltd.) using equimolar amounts of Biotin-(PEG)$_{12}$-NHS and Diisopropylethylamine.

Reaction B: Synthesis of DTPA Derivative of Di-C22-Lipid 10.7 mg of Diethylenetriaminepentaacetic (DTPA) dianhydride (Aldrich) was added in 1 ml of DMSO to dissolve the white solid, and 1 ml of 5 mg/ml Di-C22-PE in chloroform and 16 μl of diisopropylethylamine. The mixture was heated-up by immersing the vial in hot water for complete dissolution of all ingredients.

The tube was left for approximately 24 hours at a temperature of 60° C.

Thin-layer chromatography was performed to evaluate progress of reactions A and B with a stationary phase: $SiO_2$ on glass, and a mobile phase: Chloroform-Methanol 2:1 by volume.

3 μl of each of 5 mg/ml Di-C22-PE in chloroform, reaction mixture A, and 6 μl of reaction mixture B were pipetted on a start line of the chromatographic plate; dried; immersed into the container with mobile phase (below the start line) and left there until solvent front line reached approximately three quarters of the height of the chromatographic plate. The plate was dried, and then treated with Ninhydrin and heated. Characteristic of the primary amine presence, a purple spot had appeared only with di-C22-PE, but NOT with the reaction mixtures A and B, confirming that intended the conjugation had occurred as expected.

Synthesis of Europium DTPA-Derivative of Di-C22-Lipid:

1 ml of reaction mixture B was pipetted into a separate vial, and chloroform was evaporated by the Argon flow at room temperature. 550 μl of 10.04 mg/ml $EuCl_3.6H_2O$ in 0.1 M citrate buffer pH 5.20 was added to the same vial; resulting pH (measured by pH paper stick) was approximately 5.8. The vial was heated in hot water for approximately 15-20 min.

2 ml $H_2O$ and 3 ml chloroform was added to the same vial and mixed well (vortexed) to extract lipid (which is now conjugated with DTPA and complexed with Eu) into the chloroform phase. 500 μl methanol and additional 2 ml of water was added to improve phase separation.

The chloroform phase was separated and transferred into the separate vial with the known weight. Chloroform was evaporated first in the flow of the Argon, and later by lyophilization. The final weight of the Europium-DTPA-di-C22-lipid conjugate was approximately 2.5 mg.

Preparation of Biotin-(PEG)$_{12}$-Di-C22-PE.

Biotin-(PEG)$_{12}$-NHS (Quanta Biodesign, 20.2 mg) was added to di-C22-phospatidylethanolamine (16.8 mg) in chloroform in the presence of diisopropyl ethylamine (Aldrich, 7.5 μl) and incubated overnight. Chloroform was removed in a flow of nitrogen gas, reaction mixture vacuumed then lyophilized to remove excess of diisopropyl ethylamine, and re-dissolved in chloroform.

Preparation of Maleimide-(PEG)$_{12}$-PE.

Maleimide-(PEG)$_{12}$-NHS (Quanta Biodesign, 17 mg) is added to di-C22-phosphatidylethanolamine (15.3 mg) in chloroform in the presence of diisopropyl ethylamine (Aldrich, 6.9 μl) and incubated overnight. Chloroform was removed in a flow of nitrogen gas, reaction mixture vacuumed then lyophilized to remove excess of diisopropyl ethylamine, and then re-dissolved in chloroform.

Preparation of TCO-PEG12-di-C22-PE.

10 mg of di-C22-phosphatidylethanolamine (Avanti) was dissolved in 2 ml chloroform in hot water and added to a vial containing 10 mg of trans-Cyclooctene-(PEG)$_{12}$-NHS (Click Chemistry tools) and 3 μl DIPEA. After overnight incubation at 37 C chloroform was removed under vacuum, and excess of DIPEA was removed by prolonged lyophilization. Reaction completion was confirmed visually, by disappearance of amino-positive PE color after ninhydrin spray of a TLC plate. Final material was redissolved in chloroform at 2.3 mg/ml and stored in the freezer.

Example 2

Preparation of Lanthanide-Chelated Lipid Nanoparticles.

NP1: 2.5 mg di-C22-phosphatidylcholine (Avanti Polar Lipids), 2.5 mg di-C22-PE-DTPA-Eu, and 0.25 mg di-C22-PE-PEG3-biotin was mixed in a vial and fully dissolved in chloroform; chloroform was evaporated in the flow of Ar gas; residual organic solvent was removed by overnight lyophilization. Material was dispersed in 2 ml saline, and gotten off the walls of the vial and subjected to centrifugal wash in the microfuge (14,000 rpm, 10 min, 3 times) in saline to remove free water-soluble contaminants. Sediment redispersed in saline and subjected to sonication (Heat Systems W-375, 20 KHz, equipped with a microtip probe, 50% power) to disperse resulting particles to smaller size. Resulting particles, according to dynamic light scattering, had mean size 146.4 nm (Nicomp 370 DLS apparatus). Particles were stored refrigerated.

NP2: Chloroform solutions of Eu-DTPA-di-C$_{22}$-phosphatidylethanolamine and biotin-(PEG)$_{12}$-di-C$_{22}$-phosphatidylethanolamine were mixed, and chloroform evaporated in a stream of nitrogen gas. A mixture contained, e.g., 0.1 ml of 0.2 mg/ml Eu-DTPA-lipid, 1 μl, or 5 μl, or 20 μl of biotin-PEG12-di-C$_{22}$-phosphatidylethanolamine chloroform solution.

Figure 14:
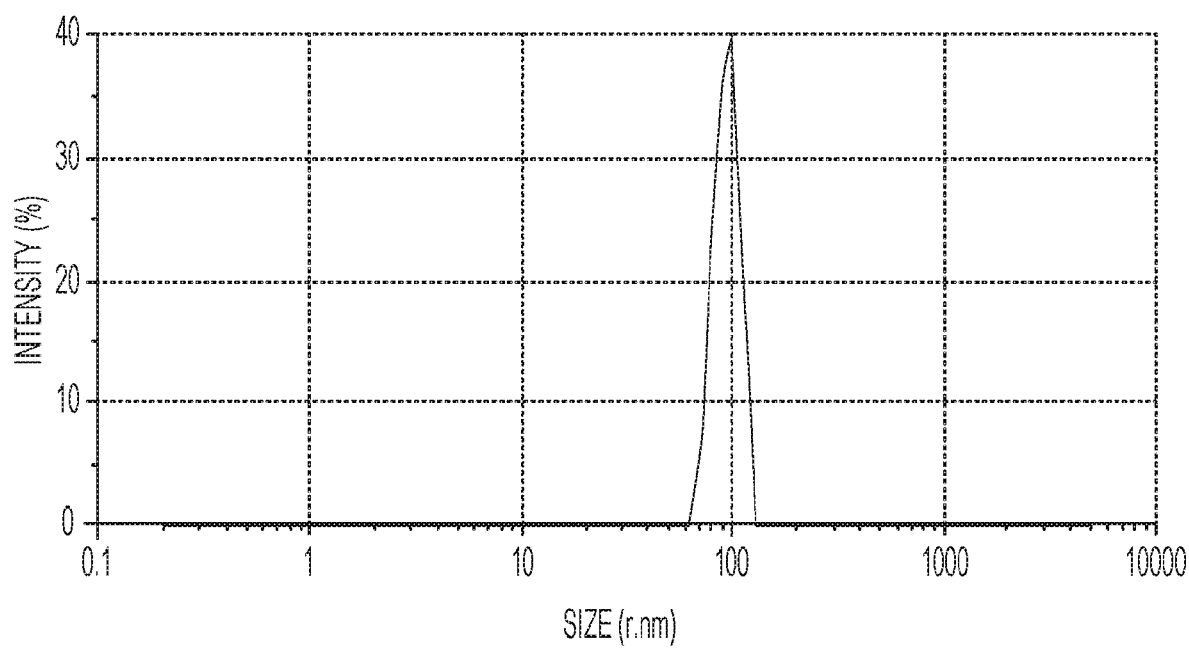
FIG. 14 shows the size distribution of NP2 nanoparticles, by radius, nm, estimated by dynamic light scattering.

Resulting dry material was substituted with normal saline solution and vortexed to remove dry lipids from the walls of the vessel. Centrifugation was used to sediment lipid particles and separate out free biotin-PEG, or maleimide-PEG, or Eu not attached to the nanoparticles. The resulting lipid particle mixture in saline was then subjected to probe-type sonication (Heat Systems Ultrasonics W-375 unit, microtip, 50% power setting) for homogenization of the metal carrier particles. Resulting particles, according to dynamic light scattering, had mean size of approximately 100 nm. See FIG. 14. Particles were stored refrigerated, and used as necessary for binding to the immunoassay reagents.

Figure 4:
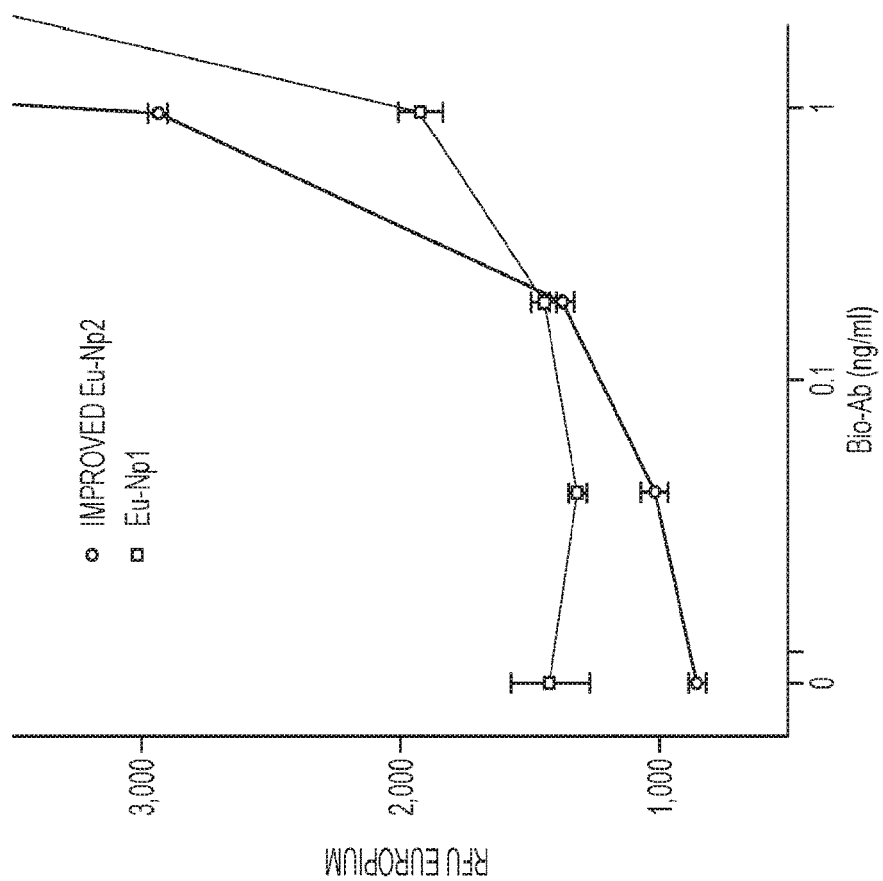
FIG. 4 shows a comparison of biotinylated particles NP1 and NP2, a lipid of the invention, binding to streptavidin bound to biotinylated antisera coated on a microtiter plate.
Figure 4:
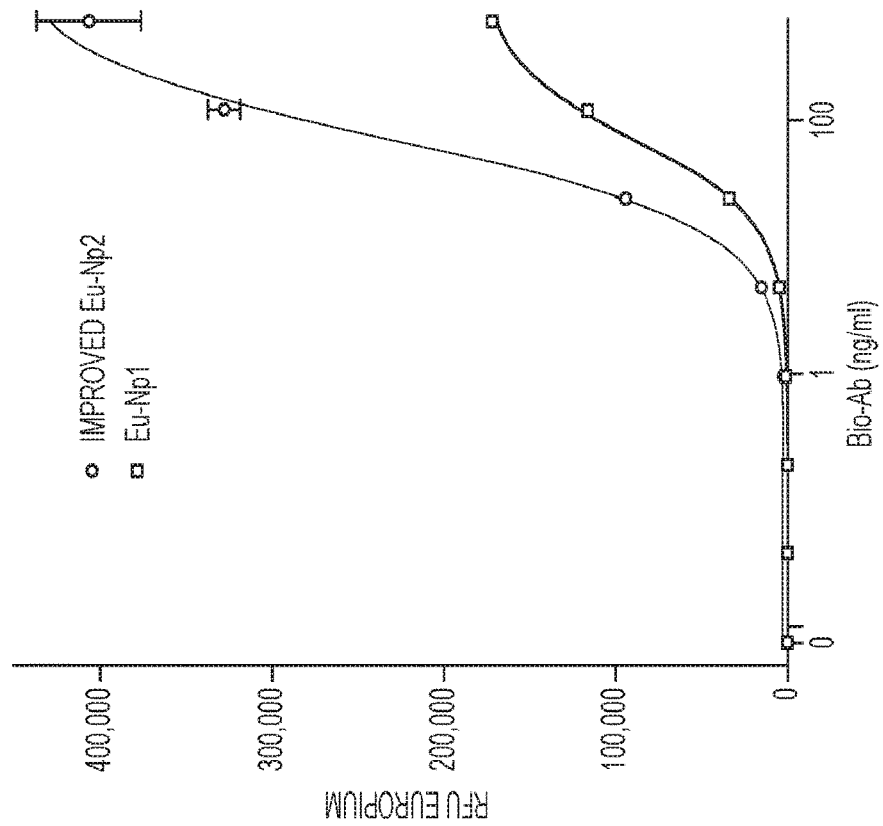

FIG. 4 shows a comparison of biotinylated particles NP1 and NP2 binding to streptavidin bound to biotinylated antisera coated on a microtiter plate. NP2 allowed for all the Eu to be bound to the particle. Twice the signal was achieved with NP2, while obtaining lower non-specific binding.

Example 3

Preparation Streptavidin Covalently Labeled with Lipid Nanoparticles 1 mg Di-C22-Phosphatidylcholine (Avanti Polar Lipids, as above) was mixed with 0.1 ml of chloroform, containing 23 µg TCO-PEG12-di-C22-PE; 0.1 ml of di-C22-PE-DTPA-Eu solution (20 µg) was added; resulting mixture was completely dissolved with the aid of hot water; chloroform was then removed in the flow of argon gas. Resulting lipid material was dispersed in 1 ml of normal saline and sonicated (as above, W-375 sonicator at 20 KHz). Resulting particles were subjected to centrifugation (14,000 g, 15 min) and supernatant discarded. Pellet of lipid particles was dispersed in 0.1 ml of normal saline, and 20 µl aliquot taken for streptavidin coupling.

Separately, 0.5 mg streptavidin (Anaspec) was dissolved in 0.5 ml of 0.1 M HEPES, pH 7.4 and added with solution of tetrazine-NHS (Click Chemistry Tools, cat #1127) in DMSO (10 mg/ml), 10 µl, mixed, and incubated overnight at 4° C. Free tetrazine was removed from the conjugate by ultrafiltration (Amicon Ultracep 100K, using three washes with 0.1M HEPES). Purified material was diluted back to 0.5 ml volume. Resulting tetrazine-protein demonstrated significant pink color, confirmed by optical density spectrophotometric measurement at 517 nm.

0.1 ml of tetrazine-streptavidin was added with 0.02 ml of the TCO-Eu-lipid particles and incubated for 15 minutes with gentle mixing. Reaction mixture was then subjected to centrifugation (14,000 rpm, Eppendorf 5415 centrifuge) for 10 min. Supernatant (that should contain free unreacted protein that did not attach to the lipid particles) was collected. To confirm successful protein coupling supernatant optical density was compared with equally diluted streptavidin-tetrazine conjugate, and resulted in an approximately 16% coupling yield.

Example 4

C-Peptide Nanoparticle Sandwich Assay with NP1

A matched pair of monoclonal antisera for a C-peptide immunoassay was purchased from Fitzgerald Industries International (North Acton, MA). Catalog #s 10-C65B (capture) and 10-C65C (reporter). The reporter antiserum was biotinylated using NHS-ester chemistry (ChromaLink) to yield 5.1 moles biotin per mole antibody (Solulink, Inc. San Diego, California).

1. C-peptide capture antiserum at 1 ug/ml in 0.05 M carbonate buffer pH 9.6, was coated in 96 well high protein binding microtiter plates, 100 µl/well, overnight at 4° C.
2. The plates were emptied and blocked with 200 µl 1% BSA in PBS (blocking buffer) per well for 1.5 hr at room temperature (RT).
3. The wells were washed 6 times with 200 µl PBS containing 0.05% Tween-20 (PBST).
4. Wells were then loaded with 100 µl of C-peptide standards or unknowns and incubated 1 hr at RT.
5. The wells were washed 6 times with 200 µl PBST.
6. 100 µl 0.5 µg/ml biotinylated reporter antisera diluted in blocking buffer was added to each well and incubate for 1.0 hr at RT.
7. The wells were washed 6 times with 200 µl PBST.
8. 100 µl 0.5 µg/ml streptavidin in biotin-free casein buffer (Fitzgerald Industries) was added to each well and incubated 30 min at RT.
9. The wells were washed 6 times with 200 µl PBST.
10. 100 µl of nanoparticle stock diluted 1:1,000 in Low-Cross Buffer (Candor Biosciences, Wangen, Germany) was added per well and incubated overnight at 4° C.
11. The wells were washed 6 times with 200 µl PBST.
12. 100 µl PerkinElmer DELFIA® enhancement solution was added per well, incubated 5 min and counted per standard Eu TRF protocol. (Manufacturer's directions for product 1244-104, DELFIA® Enhancement Solution; TRF settings: excitation filter 340 nm, delay 400 us, emission filter 615 nm, counting window 400 µs).

Figure 3:
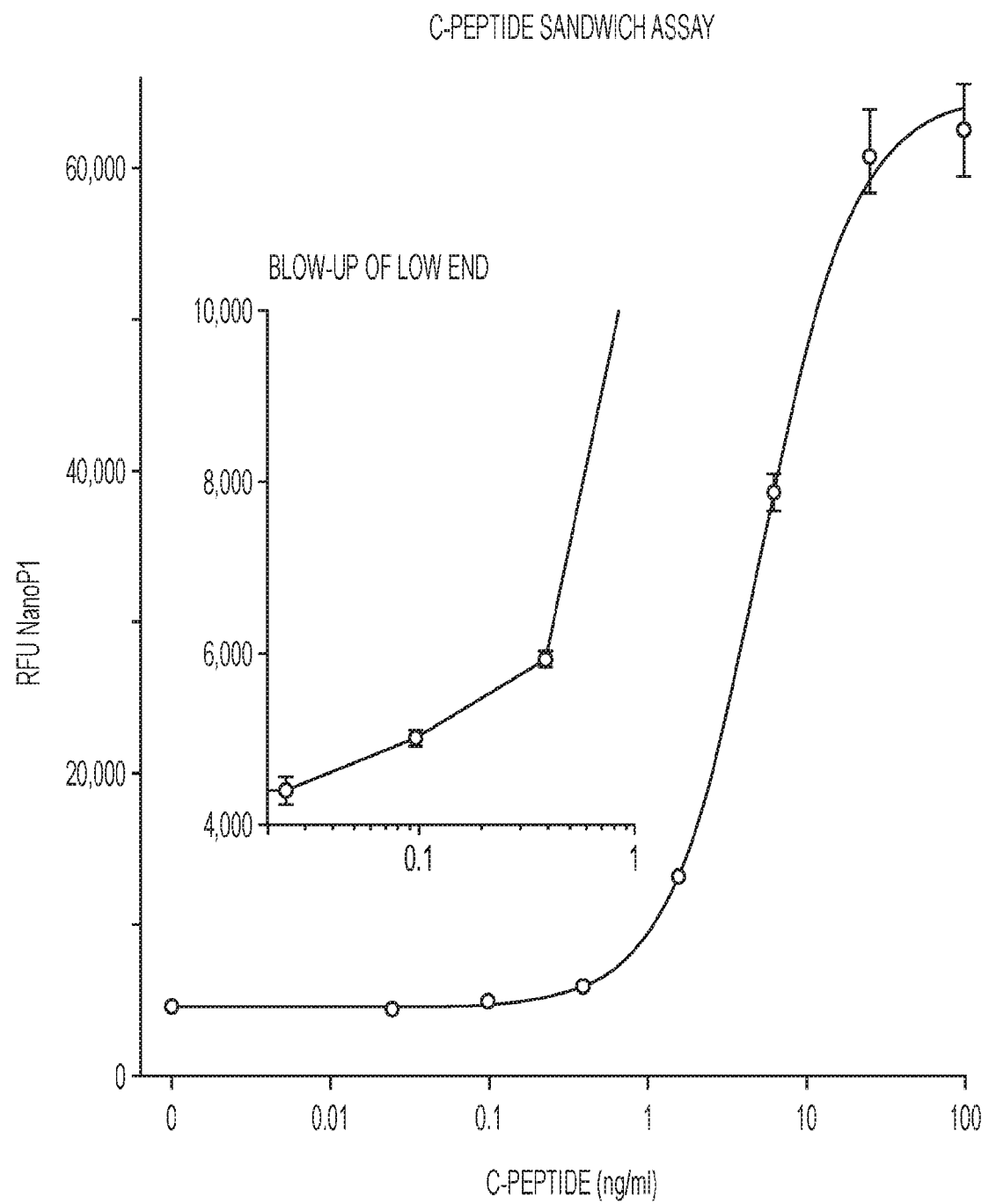
FIG. 3 shows detection of C-peptide in a sandwich assay using NP1, a lipid nanoparticle of the invention.

As shown in FIG. 3, sandwich assays using NP1 were able to detect C-peptide with good sensitivity over a high relative dynamic range.

Example 5

Dust Mite Allergen Assay with NP1

A commercial sandwich assay for dust mite antigen Der p1 supplied by Indoor Biotechnologies, Charlottesville, VA was used. The assay was performed using their suppled HRP ELISA protocol, and alternatively their biotinylated second antibody was detected by DELFIA® or nanoparticle TRF methods (using the protocol as in example 4 above).

Figure 2:
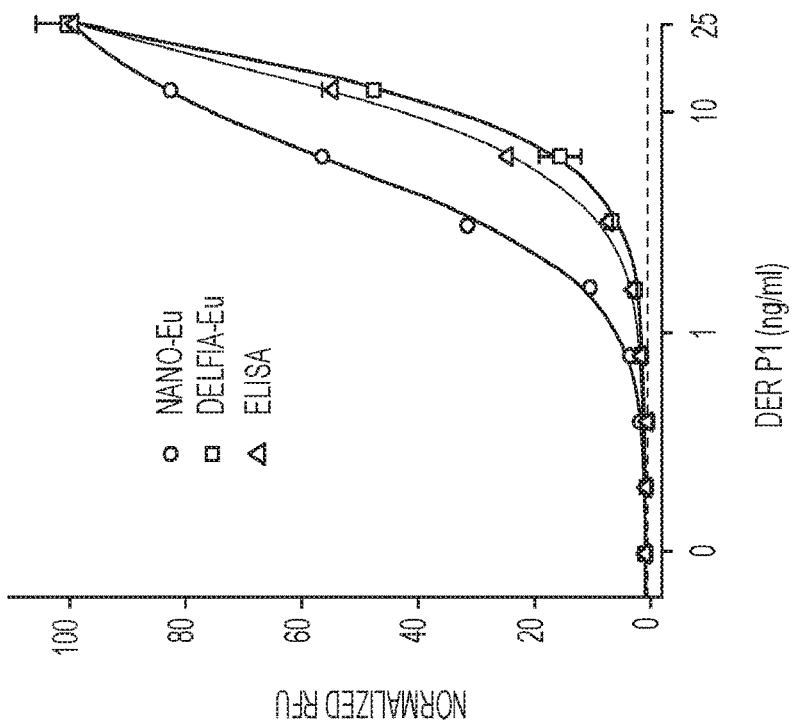
FIG. 2 shows the improved performance from the NP1 nanoparticle TRF assay: (left) compared to the currently available DELFIA® TRF technology used in a sandwich assay for ghrelin; (right) the detection of dust mite allergen in a sandwich assay using NP1, a lipid nanoparticle of the invention, compared to the DELFIA® assay or the manufacturer's standard ELISA protocol using horseradish peroxidase (HRP) and a colorimetric enzyme substrate.
Figure 2:
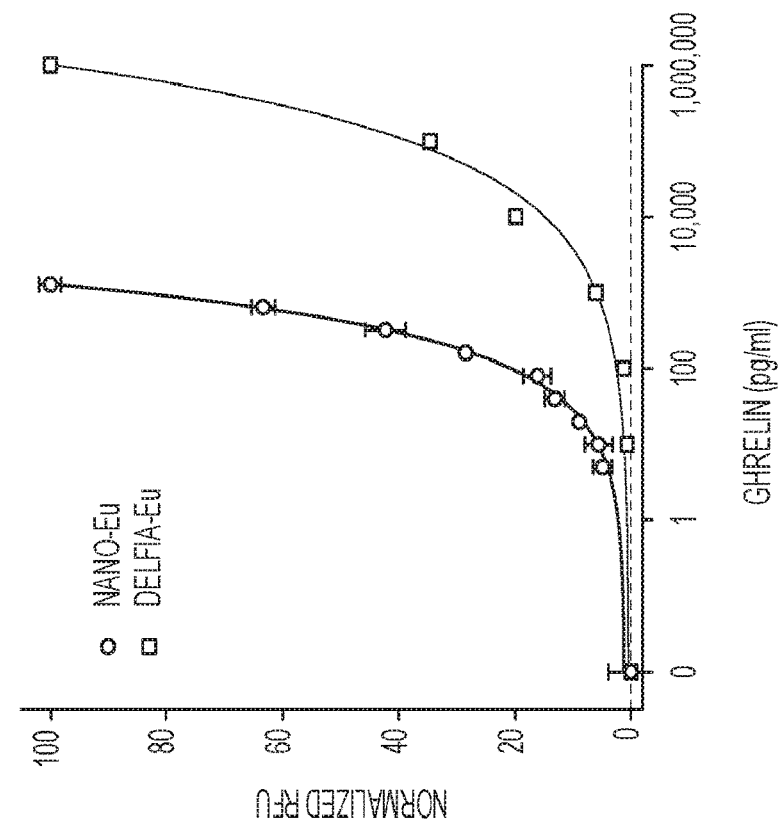

As shown in FIG. 2, the sandwich immunoassay with NP1 shows 5.5-fold better sensitivity compared to DELFIA®.

Example 6

Conversion of Mercodia Ultrasensitive C-Peptide Assay to Nanoparticle Assay

Mercodia Ultrasensitive Human C-Peptide Assay (Mercodia Ultrasensitive Human C-peptide assay Catalog No. 10-1141-01, Mercodia, Uppsala Sweden) was converted to a nanoparticle assay with improved sensitivity, range, and signal to noise ratio.

1. The standard Mercodia protocol was followed exactly up to the wash after the incubation with the enzyme conjugate.
2. In the next step, the standard Mercodia protocol was modified by adding affinity purified polyclonal rabbit anti-HRP (Jackson ImmunoResearch, West Grove, PA), 100 µl, 1 µg/ml in 1% BSA in PBS (instead of adding enzyme substrate) and incubated for 1 hr.
3. The wells were washed 6 times with 200 µl PBS containing 0.05% Tween-20 (PBST).
4. 100 µl 0.5 µg/ml streptavidin in biotin-free casein buffer (Fitzgerald Industries) was added to each well and incubated 30 min at RT.
5. The wells were washed 6 times with 200 µl PBST.
6. 100 µl of nanoparticle stock diluted 1:1,000 in Low-Cross Buffer (Candor Biosciences, Wangen, Germany) was added per well and incubated overnight at 4° C.
7. The wells were washed 6 times with 200 µl PBST.
8. 100 µl PerkinElmer DELFIA® enhancement solution was added per well, incubated 5 min and counted per standard Eu TRF protocol.

Figure 5:
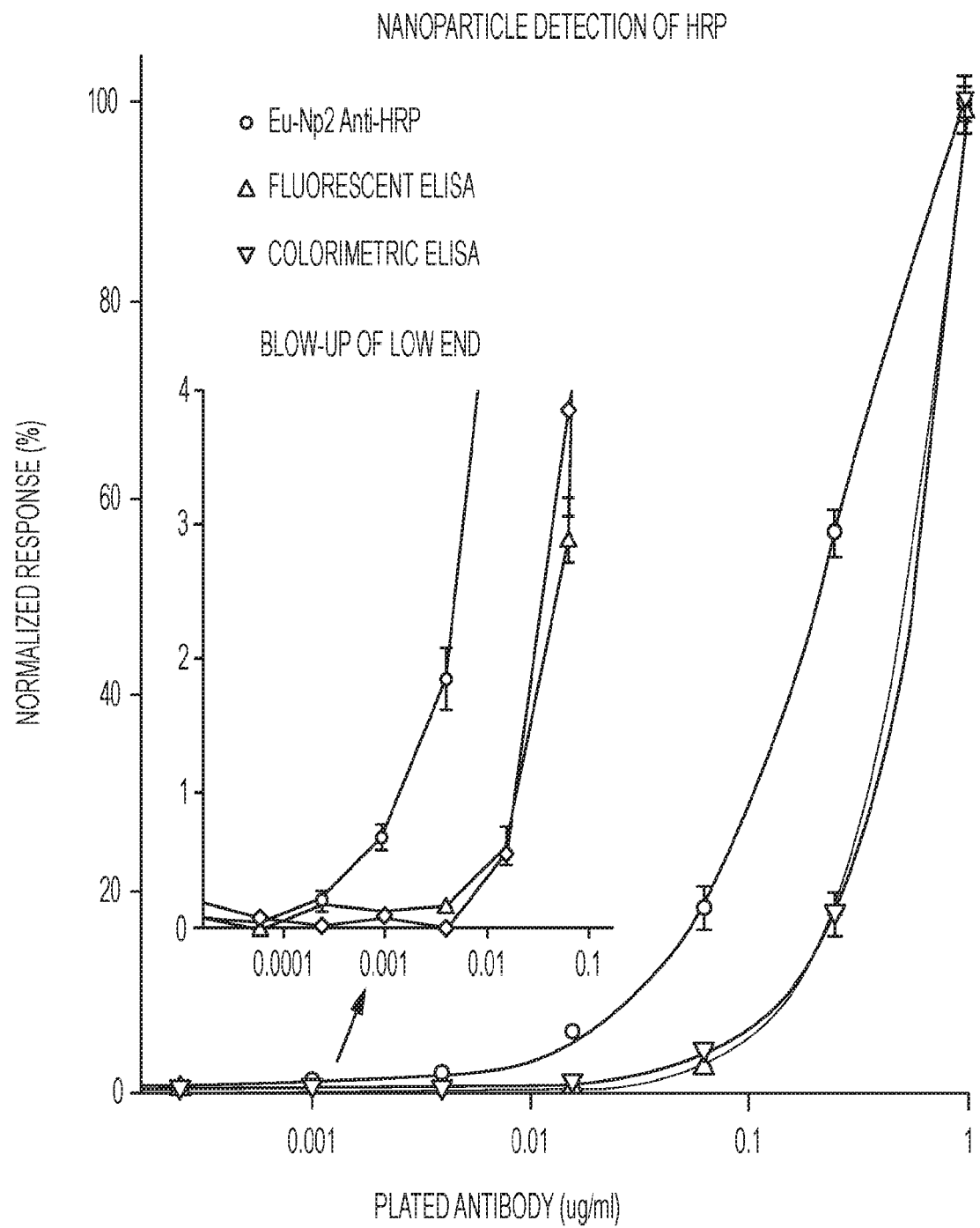
FIG. 5 shows a comparison of anti-HRP labeled with NP2, a lipid nanoparticle of the invention, fluorescent ELISA and colorimetric ELISA in detecting peroxidase labeled goat antisera to rabbit IgG coated on microtiter plates.

As shown in FIG. 5, the sandwich assay using NP2 was 40-fold more sensitive than the colorimetric ELISA and 26-fold more sensitive than the fluorescent ELISA in detecting HRP labeled antibody coated to a plate.

The lanthanide-chelate lipid nanoparticle can be linked to different commercially available antisera to HRP. Anti-HRP antisera (Jackson ImmunoResearch, West Grove, PA; 123-005-021 (goat) 323-005-021 (rabbit)) were examined. These anti-HRP affinity-purified antibodies were biotinylated using the ChromaLink biotin antibody labeling kit (Solulink San Diego, CA) and were used at a concentration of 0.5 µg/ml, incubated for 1 hr and washed before the addition of streptavidin as in example 4 above.

Figure 6:
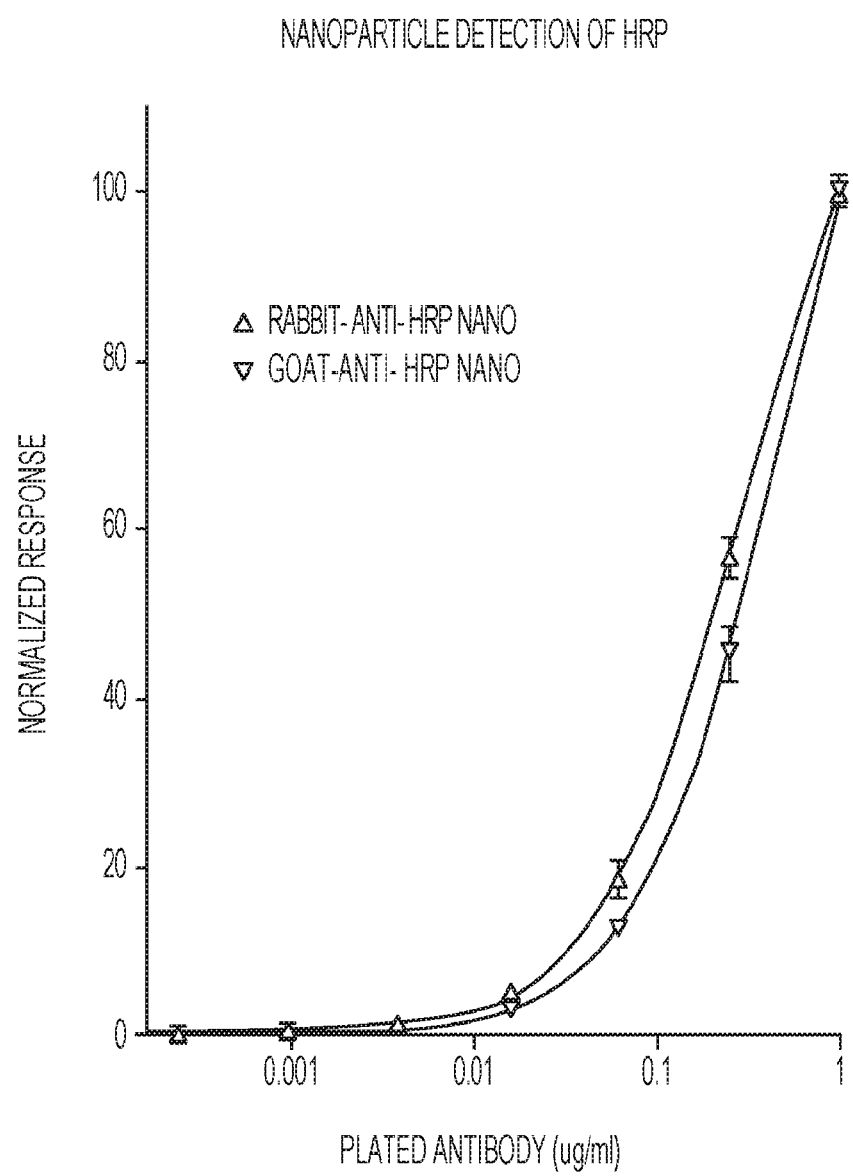
FIG. 6 shows detection of peroxidase labeled goat antisera with rabbit anti-HRP labeled with NP2 and goat anti-HRP labeled with NP2, a lipid nanoparticle of the invention.

As shown in FIG. 6, both polyclonal goat anti-HRP and polyclonal rabbit anti-HRP gave good results.

Figure 11:
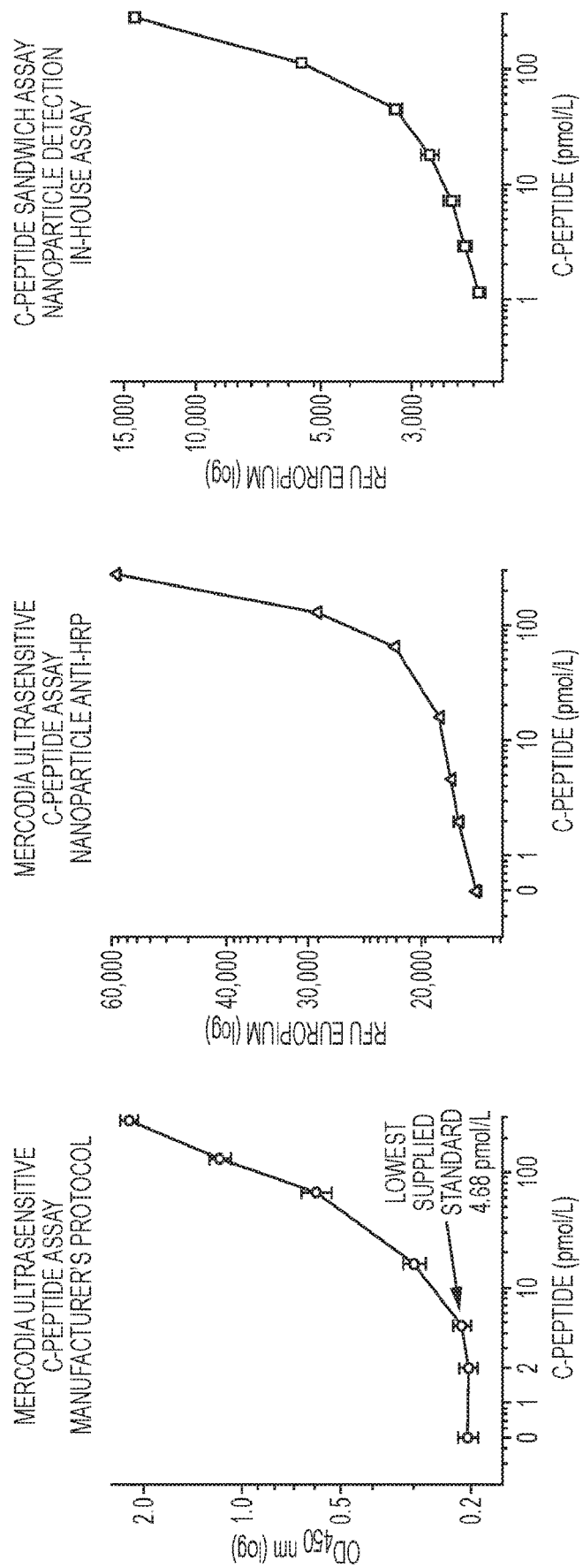
FIG. 11 shows a comparison of C-peptide detection using the manufacturer's colorimetric protocol (left), the TRF protocol modified to use an anti-HRP antibody linked to a lanthanide-chelate lipid nanoparticle (middle), and a TRF C-peptide sandwich assay in which the reporter antibody is linked to a lipid nanoparticle of the invention (right).

FIG. 11 shows a comparison of C-peptide detection using the manufacturer's colorimetric ELISA protocol (left), the protocol modified to use an anti-HRP antibody linked to a lanthanide-chelate lipid nanoparticle (middle), and a C-peptide sandwich assay from Example 2 in which the reporter antibody is linked to a lanthanide-chelate lipid nanoparticle (right).

Example 7

A polyHRP fluorescence assay was performed as reported in Liu, et al., 2008. The DELFIA® assay was performed per the manufacturer's instructions. Assays with NP1 were performed as in example 4, above.

Figure 12:
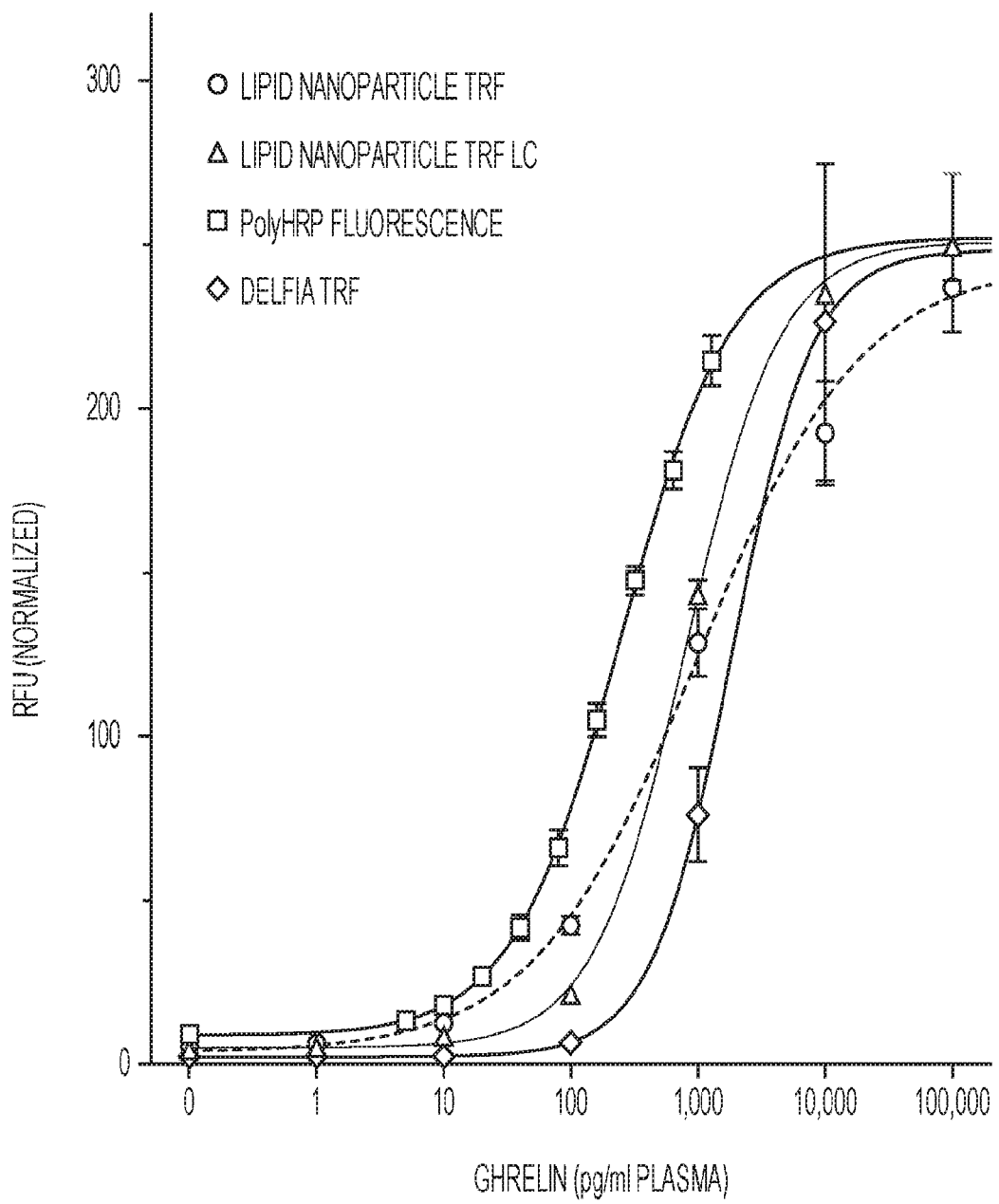
FIG. 12 shows the performance of two formulations of NP1 assay in detecting ghrelin. The formulations differ by the buffer used—Lipid Nanoparticle TRF uses a BSA buffer (circle) and Lipid Nanoparticle TRF LC uses the LowCross buffer (triangle). The plots compare the assays to a PolyHRP Fluorescent ELISA (square) and to a commercially available TRF product (DELFIA®) (diamond).

FIG. 12 shows the performance of two formulations NP1 assay in detecting ghrelin. The formulations differ by the buffer used—Lipid Nanoparticle TRF uses a BSA buffer (circle) and Lipid Nanoparticle TRF LC uses the LowCross buffer (triangle). The plots compare the assays to a PolyHRP Fluorescent ELISA (square) and to a commercially available TRF product (DELFIA®) (diamond). The assay sensitivities, EC50-s and dynamic ranges are shown in Table 1 below:

TABLE 1

| Assay | Relative Assay Sensitivity | Calculated $EC_{50}$ | Dynamic Range |
|---|---|---|---|
| Lipid Nanoparticle TRF (LNP/TRF) | 3.4 pg/ml | 1,846 pg/ml | 2,205X |
| Lipid Nanoparticle TRF LC (LNP/TRF) | 1.1 pg/ml | 815 pg/ml | 280X |
| PolyHRP Fluorescence (HRP/F) | 2.9 pg/ml | 268 pg/ml | 352X |
| DELFIA ® TRF (DELFIA ®/TRF) | 23.6 pg/ml | 878 pg/ml | 72X |

The assays using lipid nanoparticles of the invention are more sensitive and show a better relative dynamic range than the commercially available assay.

Example 8

Terbium and Europium Nanoparticles

Figure 13:
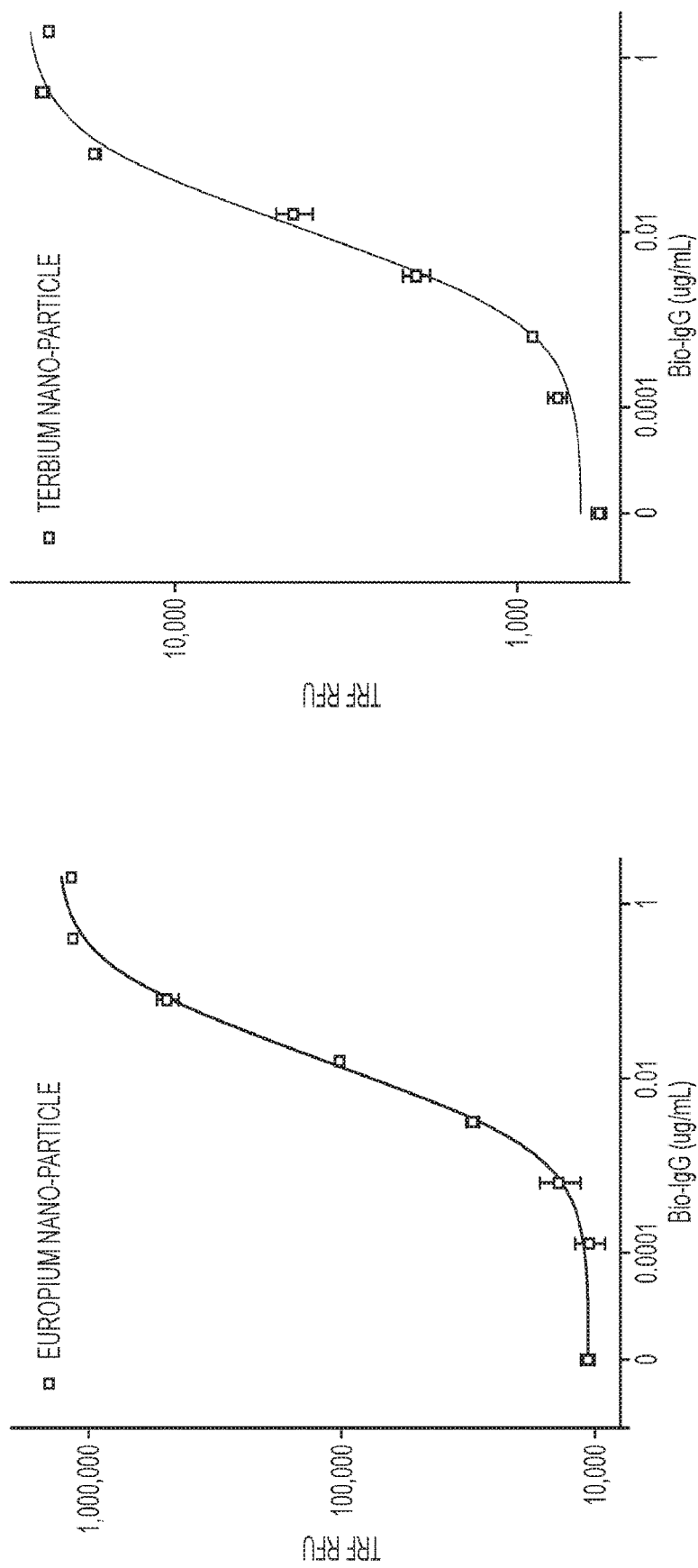
FIG. 13 shows a comparison between a Europium-chelate lipid nanoparticle and Terbium-chelate lipid nanoparticles in detecting a dilution series of biotinylated antibody coated on to the wells of a plate.

Europium and terbium were compared in parallel on the same plate using a dilution series of biotinylated antibody coated to the wells as the target to be detected. The protocol was as described in example 4 up until the TRF fluorescence detection. For Europium 100 µl PerkinElmer DELFIA® enhancement solution (product 1244-104) was used and read with TRF setting: excitation filter 340 nm, delay 400 µs, emission filter 615 nm, counting window 400 µs (as in example 4 above). For terbium 50 µl enhancement solution (1244-104) plus 50 µl terbium enhancer (PerkinElmer C500-100) was used according to manufacturer's instructions and read with excitation filter 340 nm, delay 500 µs, emission filter 545 nm, counting window 1400 µs. The difference in relative fluorescence units between europium and terbium in FIG. 13 is due to differences in filters and settings required to detect the different "colors" of the different lanthanides.

Example 9

Comparison of DELFIA® with Assays with Previously Available Fluorescent Nanoparticles The DELFIA® assay for ghrelin was performed as per the manufacturer's instructions. $Eu^{3+}$ filled Streptavidin coated beads from Molecular Probes, or Quantum Dots from Invitrogen or Torrent Dots from BioPal were bound anti-ghrelin antibodies. Polystyrene beads, binding and blocking buffers, were obtained from the authors of Nareoja, et al., 2009 using the protocol therein.

REFERENCES

1. Liu, et al., *J Clin Endocrinol Metab,* 93:1980-87 (2008).
2. Nareoja, et al., *Journal of Immunological Methods* 345: 80-89 (2009).
3. Soukka, et al., *Clinical Chemistry* 47:7 1269-1278 (2001).
4. Ge, et al, *Biophysical Journal Volume* 81, Issue 2, Pages 994-1005 (2001).
5. Gallego, et al., *BioMed Research International Volume* 2014, Article ID 129458 (2014).
6. Rundstrom, et al., *Clinical Chemistry* 53:2 342-348 (2007).

The claimed invention is:

1. A lipid nanoparticle consisting of:
    a) a plurality of phospholipids with aliphatic chains with chain lengths ranging from C19 to C50, wherein each phospholipid is attached to linker moiety, wherein the linker moiety is attached to the phospholipid via a polyethylene glycol linker, wherein the polyethylene glycol linker is $(-CH_2-CH_2-O)_n$, wherein n is an integer from 3-2000; and
    b) a plurality of phospholipids with aliphatic chains with chain lengths ranging from C19 to C50, wherein each phospholipid is attached to a lanthanide chelate, wherein the lanthanide chelate consists of:
        (i) a lanthanide ion selected from the group consisting of $Eu^{3+}$, $Tb^{3+}$, $Sm^{3+}$, and $Dy^{3+}$; and
        (ii) a chelating agent.

2. The lipid nanoparticle of claim 1, wherein the phospholipids of components a) and b) are independently selected from phosphatidylethanolamine, phosphatidylcholine, and mixtures thereof.

3. The lipid nanoparticle of claim 1, wherein the chain lengths of the aliphatic chains of the phospholipids range from C22 to C38.

4. The lipid nanoparticle of claim 1, wherein the linker moiety or is either a covalent linker moiety or biotin.

5. The lipid nanoparticle of claim 4, wherein the linker moiety is a covalent linker moiety selected from the group consisting of maleimide, vinylsulfone, thiopyridine, isothiocyanate, aldehyde, trans-cyclooctene, dibenzoyclooctyl, azide, alkyne, imidazolylcarbonyl, tetrazine, thiol, iodoacetamido, bromoacetamido, succinimidyl, pentachlorophenyl, tetrafluorophenyl, and sulfosuccinimdyl.

6. The lipid nanoparticle of claim 1, wherein the chelating agent is selected from the group consisting of diethylenetriamine pentaacetic acid (DTPA), ethylenediamine tetraacetic acid (EDTA), triethylenetetraminehexaacetic acid (TTHA), 1,4,7,10-tetraazacyclododecane-1,4,7,10-tetraacetic acid (DOTA), 1,4,7-triazacyclononane-N,N',N"-triacetic acid (NOTA), deferoxamine, diethylenetriamine penta(methylene phosphonic acid) (DTPMP), 1,4,7,10-tetraaza-1,4,7,10-tetra(2-carbamoylmethyl)cyclododecane (TCMC), 1,4,7,10-tetraazacyclododecane-1,4,7-tri (carbamoylmethyl)-10-acetic acid (DOTAM), 2-[1,4,7,10-tetraazacyclododecane-4,7,10-tris(t-butyl acetate)]-pentanedioic acid (DOTAGA), 1,4,8,11-tetraazacyclotetradecane-1,4,8-triacetic acid (DO3A), tetraazabicyclopentadecatrienetriacetic acid (PCTA), and 1,4,7-triazacyclononane-1,4-bis(acetic acid) (NO2A).

7. The lipid nanoparticle of claim 4 wherein the linker moiety is biotin, and the chelating agent is DTPA.

8. The lipid nanoparticle of claim 1, wherein the lanthanide is $Eu^{3+}$ or $Tb^{3+}$.

9. A labeled antibody, wherein the antibody is polyclonal or monoclonal, and is linked to the lipid nanoparticle of claim 1.

10. The labeled antibody of claim 9, wherein the antibody is an antigen binding fragment selected from Fab, Fab', (Fab')$_2$, or Fv fragment, or is a single chain antibody.

11. The labeled antibody of claim 9, wherein the antibody is covalently linked to the lipid nanoparticle.

12. The labeled antibody of claim 9, wherein the antibody is biotinylated and the linker moiety of the nanoparticle is biotin, and wherein said antibody and said nanoparticle are crosslinked with streptavidin.

13. The labeled antibody of claim 9, wherein the antibody is an anti-HRP antibody.

14. A labeled streptavidin, wherein streptavidin is covalently or noncovalently linked to the nanoparticle of claim 1.

15. The labeled streptavidin of claim 14, wherein the linker moiety on the lipid nanoparticle is biotin, and the streptavidin is non-covalently bound to the lipid nanoparticle.

16. A time-resolved fluorescence bioaffinity assay to determine the presence or concentration of an analyte in a sample comprising the steps of:
    a) mixing the sample with a labeled reagent, wherein the labeled reagent is a reagent linked to a lipid nanoparticle of claim 1;
    b) reacting the analyte with the labeled reagent, wherein a bioaffinity reaction between the analyte and the labeled reagent takes place resulting in a reaction product, wherein the analyte is bound to the labeled reagent;
    c) separating said reaction product from unbound labeled reagents, and
    d) measuring the amount of lanthanide from the reaction product by time-resolved fluorescence.

17. A time-resolved fluorescence bioaffinity assay to simultaneously determine the presence or concentration of two to four analytes within a sample comprising the steps of:
    a) mixing the sample with two to four analyte-specific labeled reagents, wherein each labeled reagent is linked to a lipid nanoparticle of claim 1, each with a different lanthanide;
    b) reacting the analytes with the analyte-specific labeled reagents, wherein specific bioaffinity reactions between the analytes and their corresponding labeled reagents takes place, resulting in two to four reaction products, wherein each analyte is its specific labeled reagent,
    c) separating said reaction products from unbound labeled reagents, and
    d) measuring the amount of lanthanide from the reaction products by time-resolved fluorescence.

18. A time-resolved fluorescence sandwich immunoassay to determine the presence or concentration of an analyte in a sample comprising the steps of:
    mixing the sample with a capture antibody immobilized on a surface, an HRP-conjugated reporter antibody and a labeled antibody of claim 13;
    forming an ordered quaternary complex comprising the capture antibody, analyte, HRP-conjugated reporter antibody, and the labeled antibody of claim 13; and
    detecting the amount of lanthanide retained on the surface.

19. The lipid nanoparticle of claim 1, wherein:
    a) is biotin-(PEG)$_3$-di-C22-phosphatidylethanolamine and b) is Eu-DTPA-di-C22-phosphatidylethanolamine; or
    a) is biotin-(PEG)$_{12}$-di-C22-phosphatidylethanolamine or TCO-(PEG)$_{12}$-di-C22-phosphatidylethanolamine and b) is Eu-DTPA-di-C22-phosphatidylethanolamine.

20. A time-resolved fluorescence bioaffinity assay wherein a labeled reagent is used to determine the presence or concentration of an analyte in a sample, the improvement wherein the label in the labeled reagent is a lipid nanoparticle of claim 1.

21. A time-resolved fluorescence sandwich immunoassay to determine the presence or concentration of an analyte in a sample comprising the steps of:
    mixing the sample with a capture antibody immobilized on a surface, and a biotinylated reporter antibody;
    forming an ordered ternary complex comprising the capture antibody, the analyte, and the biotinylated reporter antibody;
    adding a streptavidin;
    forming an ordered quaternary complex comprising the capture antibody, the analyte, the biotinylated reporter antibody, and the streptavidin;
    adding a lipid nanoparticle of claim 7;
    forming an ordered quinary complex comprising the capture antibody, the analyte, the biotinylated reporter antibody, the streptavidin, and the lipid nanoparticle; and
    detecting the amount of lanthanide retained on the surface.

* * * * *